(12) United States Patent
Krieger et al.

(10) Patent No.: US 11,523,924 B2
(45) Date of Patent: Dec. 13, 2022

(54) MEDICAL CANNULAE, DELIVERY SYSTEMS AND METHODS

(71) Applicant: Cook Medical Technologies LLC, Bloomington, IN (US)

(72) Inventors: Joshua Frye Krieger, Topsfield, MA (US); Melissa Lonn, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 567 days.

(21) Appl. No.: 16/450,070

(22) Filed: Jun. 24, 2019

(65) Prior Publication Data

US 2019/0307590 A1 Oct. 10, 2019

Related U.S. Application Data

(63) Continuation of application No. 15/140,028, filed on Apr. 27, 2016, now Pat. No. 10,327,933.
(Continued)

(51) Int. Cl.
*A61F 2/966* (2013.01)
*A61M 25/00* (2006.01)
(Continued)

(52) U.S. Cl.
CPC ........ *A61F 2/966* (2013.01); *A61B 17/00234* (2013.01); *A61B 17/3421* (2013.01);
(Continued)

(58) Field of Classification Search
CPC .......... A61M 25/0138; A61M 25/0054; A61M 25/0013; A61F 2/966; A61F 2250/0018;
(Continued)

(56) References Cited

U.S. PATENT DOCUMENTS

| 4,781,186 A | 11/1988 | Simpson et al. |
| 5,053,004 A | 10/1991 | Markel et al. |

(Continued)

FOREIGN PATENT DOCUMENTS

| AT | 506914 | 11/2010 |
| AT | 518559 | 6/2018 |

(Continued)

OTHER PUBLICATIONS

United States Patent and Trademark Office Non-Final Office Action, dated Nov. 14, 2019, pp. 1-19.
(Continued)

*Primary Examiner* — Phong Son H Dang
(74) *Attorney, Agent, or Firm* — MacMillan, Sobanski & Todd, LLC

(57) ABSTRACT

The disclosure relates to cannulae, delivery systems, methods of making cannulae, and methods of making delivery systems. A delivery system comprises an elongate outer tubular member defining an outer tubular member lumen, a cannula having a circumferential wall extending between a proximal end and a distal end and defining an interior lumen, and an intraluminal medical device disposed within the outer tubular member lumen distal to the cannula and not about the cannula. A pattern of openings arranged in an interrupted spiral extends circumferentially along the cannula.

20 Claims, 14 Drawing Sheets

Related U.S. Application Data

(60) Provisional application No. 62/153,814, filed on Apr. 28, 2015.

(51) Int. Cl.
*A61M 25/01* (2006.01)
*A61B 17/34* (2006.01)
*A61B 17/00* (2006.01)
*A61F 2/95* (2013.01)

(52) U.S. Cl.
CPC ..... *A61B 17/3468* (2013.01); *A61M 25/0013* (2013.01); *A61M 25/0054* (2013.01); *A61M 25/0138* (2013.01); *A61B 2017/00309* (2013.01); *A61B 2017/00336* (2013.01); *A61F 2/95* (2013.01); *A61F 2250/0018* (2013.01)

(58) Field of Classification Search
CPC .......... A61B 17/00234; A61B 17/3468; A61B 17/3421; A61B 2017/00336; A61B 2017/00309
See application file for complete search history.

(56) References Cited

U.S. PATENT DOCUMENTS

| | | | |
|---|---|---|---|
| 5,195,962 A | 3/1993 | Martin et al. | |
| 5,228,441 A | 7/1993 | Lundquist | |
| 5,284,128 A | 2/1994 | Hart | |
| 5,315,996 A | 5/1994 | Lundquist | |
| 5,322,064 A | 6/1994 | Lundquist | |
| 5,322,505 A | 6/1994 | Krause et al. | |
| 5,329,923 A | 7/1994 | Lundquist | |
| 5,425,723 A | 6/1995 | Wang | |
| 5,454,787 A | 10/1995 | Lundquist | |
| 5,460,187 A | 10/1995 | Daigle et al. | |
| 5,477,856 A | 12/1995 | Lundquist | |
| 5,507,766 A | 4/1996 | Kugo et al. | |
| 5,573,520 A | 11/1996 | Schwartz et al. | |
| 5,605,543 A | 2/1997 | Swanson | |
| 5,685,868 A | 11/1997 | Lundquist | |
| 5,741,429 A | 4/1998 | Donadio et al. | |
| 5,755,714 A | 5/1998 | Murphy-Chutorian | |
| 5,833,692 A | 11/1998 | Cesarini et al. | |
| 5,897,533 A | 4/1999 | Glickman | |
| 5,922,003 A | 7/1999 | Anctil et al. | |
| 6,059,769 A | 5/2000 | Lunn et al. | |
| 6,102,890 A | 8/2000 | Stivland et al. | |
| 6,146,373 A | 11/2000 | Cragg et al. | |
| 6,228,073 B1 | 5/2001 | Noon et al. | |
| 6,246,914 B1 | 6/2001 | de la Rama et al. | |
| 6,273,404 B1 | 8/2001 | Holman et al. | |
| 6,286,555 B1 | 9/2001 | Paulker et al. | |
| 6,350,253 B1 | 2/2002 | Deniega et al. | |
| 6,428,489 B1 | 8/2002 | Jacobsen et al. | |
| 6,611,720 B2 | 8/2003 | Hata et al. | |
| 6,623,491 B2 | 9/2003 | Thompson | |
| 6,652,508 B2 | 11/2003 | Griffin et al. | |
| 6,749,560 B1 | 6/2004 | Konstorum et al. | |
| 6,780,151 B2 | 8/2004 | Grabover et al. | |
| 6,860,898 B2 | 3/2005 | Stack et al. | |
| 7,001,369 B2 | 2/2006 | Griffin | |
| 7,171,275 B2 | 1/2007 | Hata et al. | |
| 7,276,062 B2 | 10/2007 | McDaniel et al. | |
| 7,540,865 B2 | 6/2009 | Griffin et al. | |
| 7,637,903 B2 | 12/2009 | Lentz et al. | |
| RE41,475 E | 8/2010 | Grabover et al. | |
| 7,850,623 B2 | 12/2010 | Griffin et al. | |
| 7,878,984 B2 | 2/2011 | Jacobsen et al. | |
| 7,914,467 B2 | 3/2011 | Layman et al. | |
| 7,918,819 B2 | 4/2011 | Karmarkar et al. | |
| 7,989,042 B2 | 8/2011 | Obara et al. | |
| 8,007,434 B2 | 8/2011 | Olson | |
| 8,048,004 B2 | 11/2011 | Davis et al. | |
| 8,048,060 B2 | 11/2011 | Griffin et al. | |
| 8,083,788 B2 * | 12/2011 | Acosta | A61F 2/91 623/1.11 |
| 8,092,444 B2 | 1/2012 | Lentz et al. | |
| 8,105,246 B2 | 1/2012 | Voeller et al. | |
| 8,182,465 B2 | 5/2012 | Griffin et al. | |
| 8,231,551 B2 | 7/2012 | Griffin et al. | |
| 8,257,279 B2 | 9/2012 | Davis et al. | |
| 8,262,563 B2 | 9/2012 | Bakos et al. | |
| 8,292,827 B2 | 10/2012 | Musbach | |
| 8,376,961 B2 | 2/2013 | Layman et al. | |
| 8,409,114 B2 | 4/2013 | Pains | |
| 8,636,716 B2 | 1/2014 | Griffin et al. | |
| 8,679,150 B1 | 3/2014 | Janardhan et al. | |
| 8,684,953 B2 | 4/2014 | Cabiri | |
| 8,690,907 B1 | 4/2014 | Janardhan et al. | |
| 8,702,781 B2 * | 4/2014 | Acosta | A61M 25/0075 623/1.11 |
| 8,715,314 B1 | 5/2014 | Janardhan et al. | |
| 8,715,315 B1 | 5/2014 | Janardhan et al. | |
| 8,715,316 B1 | 5/2014 | Janardhan et al. | |
| 8,715,317 B1 | 5/2014 | Janardhan et al. | |
| 8,721,677 B1 | 5/2014 | Janardhan et al. | |
| 8,728,010 B2 | 5/2014 | Hirshman | |
| 8,728,116 B1 | 5/2014 | Janardhan et al. | |
| 8,728,117 B1 | 5/2014 | Janardhan et al. | |
| 8,733,618 B1 | 5/2014 | Janardhan et al. | |
| 8,735,777 B1 | 5/2014 | Janardhan et al. | |
| 8,747,432 B1 | 6/2014 | Janardhan et al. | |
| 2001/0032007 A1 | 10/2001 | Hata et al. | |
| 2003/0023142 A1 | 1/2003 | Grabover et al. | |
| 2004/0039326 A1 | 2/2004 | Hata et al. | |
| 2004/0097880 A1 | 5/2004 | Schur | |
| 2004/0111044 A1 | 6/2004 | Davis et al. | |
| 2004/0181174 A2 | 9/2004 | Davis et al. | |
| 2004/0193140 A1 | 9/2004 | Griffin et al. | |
| 2005/0043682 A1 | 2/2005 | Kucklick et al. | |
| 2005/0125053 A1 | 6/2005 | Yachia et al. | |
| 2005/0177131 A1 | 8/2005 | Lentz et al. | |
| 2005/0177132 A1 | 8/2005 | Lentz et al. | |
| 2005/0267444 A1 | 12/2005 | Griffin et al. | |
| 2005/0288764 A1 * | 12/2005 | Snow | A61F 2/95 623/1.11 |
| 2006/0000434 A1 | 1/2006 | Yoshijima et al. | |
| 2006/0004346 A1 | 1/2006 | Begg | |
| 2006/0100687 A1 | 5/2006 | Fahey et al. | |
| 2006/0121218 A1 | 6/2006 | Obara et al. | |
| 2006/0142732 A1 | 6/2006 | Karmarkar et al. | |
| 2006/0200047 A1 | 9/2006 | Galdonik | |
| 2007/0049902 A1 | 3/2007 | Griffin et al. | |
| 2007/0100285 A1 | 5/2007 | Griffin et al. | |
| 2007/0112331 A1 | 5/2007 | Weber et al. | |
| 2007/0135763 A1 | 6/2007 | Musbach et al. | |
| 2007/0208224 A1 | 9/2007 | Olson | |
| 2007/0208405 A1 | 9/2007 | Goodin et al. | |
| 2007/0287955 A1 | 12/2007 | Layman et al. | |
| 2008/0021347 A1 | 1/2008 | Jacobsen et al. | |
| 2008/0021348 A1 | 1/2008 | Jacobsen et al. | |
| 2008/0021400 A1 | 1/2008 | Jacobsen et al. | |
| 2008/0021401 A1 | 1/2008 | Jacobsen et al. | |
| 2008/0021402 A1 | 1/2008 | Jacobsen et al. | |
| 2008/0021403 A1 | 1/2008 | Jacobsen et al. | |
| 2008/0021404 A1 | 1/2008 | Jacobsen et al. | |
| 2008/0021405 A1 | 1/2008 | Jacobsen et al. | |
| 2008/0021406 A1 | 1/2008 | Jacobsen et al. | |
| 2008/0021407 A1 | 1/2008 | Jacobsen et al. | |
| 2008/0021408 A1 | 1/2008 | Jacobsen et al. | |
| 2008/0077049 A1 | 3/2008 | Hirshman | |
| 2008/0077085 A1 | 3/2008 | Eidenschink et al. | |
| 2008/0086047 A1 | 4/2008 | McDaniel et al. | |
| 2008/0097398 A1 | 4/2008 | Mitelberg et al. | |
| 2008/0294231 A1 | 11/2008 | Aguilar et al. | |
| 2009/0036832 A1 | 2/2009 | Skujins et al. | |
| 2009/0036833 A1 | 2/2009 | Parins | |
| 2009/0036834 A1 | 2/2009 | Voeller et al. | |
| 2009/0043228 A1 | 2/2009 | Northrop et al. | |
| 2009/0043283 A1 | 2/2009 | Turnlund et al. | |
| 2009/0043372 A1 | 2/2009 | Northrop et al. | |
| 2009/0177040 A1 | 7/2009 | Lyons et al. | |
| 2009/0192584 A1 | 7/2009 | Gerdts et al. | |

(56) References Cited

U.S. PATENT DOCUMENTS

| | | |
|---|---|---|
| 2009/0227983 A1 | 9/2009 | Griffin et al. |
| 2009/0254000 A1 | 10/2009 | Layman et al. |
| 2010/0010299 A1 | 1/2010 | Bakos et al. |
| 2010/0036364 A1 | 2/2010 | Wubbeling |
| 2010/0063479 A1 | 3/2010 | Merdan et al. |
| 2010/0069882 A1 | 3/2010 | Jennings et al. |
| 2010/0100073 A1 | 4/2010 | Lentz et al. |
| 2010/0145308 A1 | 6/2010 | Layman et al. |
| 2010/0204774 A1 | 8/2010 | Goodin et al. |
| 2011/0022069 A1 | 1/2011 | Mitusina |
| 2011/0082443 A1 | 4/2011 | Griffin et al. |
| 2011/0251519 A1 | 10/2011 | Romoscanu |
| 2011/0276034 A1 | 11/2011 | Tomarelli et al. |
| 2012/0053419 A1 | 3/2012 | Bloom |
| 2012/0157935 A1 | 6/2012 | Wuebbeling et al. |
| 2012/0232527 A1 | 9/2012 | Griffin et al. |
| 2012/0265229 A1 | 10/2012 | Rottenberg et al. |
| 2013/0017290 A1 | 1/2013 | Sawamura |
| 2013/0046285 A1 | 2/2013 | Griffin et al. |
| 2013/0072904 A1 | 3/2013 | Musbach et al. |
| 2013/0123768 A1 | 5/2013 | Harlan |
| 2013/0296718 A1 | 11/2013 | Ranganathan et al. |
| 2013/0304034 A1 | 11/2013 | Cabiri |
| 2013/0304035 A1 | 11/2013 | Cabiri |
| 2014/0025086 A1 | 1/2014 | Rottenberg et al. |
| 2014/0031843 A1 | 1/2014 | Rottenberg et al. |
| 2014/0039398 A1 | 2/2014 | Rottenberg et al. |
| 2014/0053940 A1 | 2/2014 | Konstorum et al. |
| 2014/0121590 A1 | 5/2014 | Degen |
| 2014/0148793 A1 | 5/2014 | Griffin et al. |
| 2015/0297863 A1 | 10/2015 | Hannon et al. |
| 2015/0342580 A1 | 12/2015 | Clancy |

FOREIGN PATENT DOCUMENTS

| | | |
|---|---|---|
| AU | 2005202575 | 1/2006 |
| CA | 2520175 | 11/2004 |
| CA | 2638064 | 5/2007 |
| CA | 2633048 | 6/2007 |
| CA | 2644945 | 9/2007 |
| CA | 2645020 | 9/2007 |
| CA | 2660542 | 2/2008 |
| CA | 2694827 | 2/2009 |
| CA | 2732876 | 2/2010 |
| CA | 2736752 | 3/2010 |
| CA | 2493013 | 7/2011 |
| CA | 2694830 | 3/2016 |
| CA | 2695370 | 5/2016 |
| CA | 2769037 | 10/2017 |
| CN | 101815553 | 4/2013 |
| CN | 102215896 | 7/2013 |
| DE | 10052679 | 5/2001 |
| DE | 10308902 | 7/2013 |
| EP | 0315290 | 5/1989 |
| EP | 0937481 | 8/1999 |
| EP | 1656963 | 5/2006 |
| EP | 1457224 | 7/2008 |
| EP | 1545680 | 9/2010 |
| EP | 2056743 | 4/2011 |
| EP | 1940498 | 7/2011 |
| EP | 1968678 | 8/2011 |
| EP | 2364746 | 9/2011 |
| EP | 2183015 | 1/2012 |
| EP | 1768732 | 6/2012 |
| EP | 2183013 | 3/2013 |
| EP | 2185232 | 10/2013 |
| EP | 2762189 | 1/2014 |
| EP | 1954330 | 9/2014 |
| EP | 2456497 | 12/2014 |
| EP | 1606002 | 1/2018 |
| EP | 2473123 | 1/2019 |
| GB | 2456165 | 7/2009 |
| IL | 149828 | 9/2007 |
| JP | 2001161631 | 6/2001 |
| JP | 2003250762 | 9/2003 |
| JP | 2004275765 | 10/2004 |
| JP | 20040275765 | 10/2004 |
| JP | 2005533594 | 11/2005 |
| JP | 2006513799 | 4/2006 |
| JP | 3869644 | 10/2006 |
| JP | 2007521877 | 8/2007 |
| JP | 4184833 | 9/2008 |
| JP | 2009515656 | 4/2009 |
| JP | 2009519103 | 5/2009 |
| JP | 2009528903 | 8/2009 |
| JP | 2009528907 | 8/2009 |
| JP | 2010501273 | 1/2010 |
| JP | 2010029736 | 2/2010 |
| JP | 4583783 | 9/2010 |
| JP | 4602080 | 10/2010 |
| JP | 2010535094 | 11/2010 |
| JP | 2010535583 | 11/2010 |
| JP | 2010535587 | 11/2010 |
| JP | 2010535588 | 11/2010 |
| JP | 4686196 | 5/2011 |
| JP | 2011529757 | 12/2011 |
| JP | 2012502743 | 2/2012 |
| JP | 2012515024 | 7/2012 |
| JP | 2012533374 | 12/2012 |
| JP | 5202328 | 6/2013 |
| JP | 5441100 | 12/2013 |
| JP | 5464654 | 1/2014 |
| WO | WO1999011313 | 3/1999 |
| WO | WO2002055146 | 7/2002 |
| WO | WO2003099165 | 12/2003 |
| WO | WO2004011076 | 6/2004 |
| WO | WO2004093957 | 11/2004 |
| WO | WO2004045672 | 2/2005 |
| WO | WO2005025667 | 3/2005 |
| WO | WO2006009588 | 1/2006 |
| WO | WO2006058234 | 9/2006 |
| WO | WO2005076820 | 11/2006 |
| WO | WO2007050718 | 5/2007 |
| WO | WO2007059212 | 5/2007 |
| WO | WO2007070235 | 6/2007 |
| WO | WO2007103661 | 9/2007 |
| WO | WO2007103678 | 9/2007 |
| WO | WO2008024597 | 2/2008 |
| WO | WO2009018457 | 2/2009 |
| WO | WO2009020832 | 2/2009 |
| WO | WO2009020836 | 2/2009 |
| WO | WO2009020954 | 2/2009 |
| WO | WO2009020961 | 2/2009 |
| WO | WO2009020962 | 2/2009 |
| WO | WO2009087345 | 7/2009 |
| WO | WO2009126656 | 10/2009 |
| WO | WO10081187 | 1/2010 |
| WO | WO2010009070 | 1/2010 |
| WO | WO2010015676 | 2/2010 |
| WO | WO2010033541 | 3/2010 |
| WO | WO2011008538 | 1/2011 |
| WO | WO11028632 | 3/2011 |
| WO | WO2011009884 | 7/2011 |
| WO | WO2012027383 | 3/2012 |
| WO | WO2012141748 | 10/2012 |
| WO | WO2012141749 | 10/2012 |
| WO | WO2012141747 | 3/2013 |
| WO | WO2013164682 | 11/2013 |
| WO | WO2013173197 | 11/2013 |
| WO | WO2014030437 | 2/2014 |
| WO | WO2016176393 | 11/2016 |

OTHER PUBLICATIONS

European Patent Office, Extended European Search Report for Application No. EP17178169, dated Nov. 13, 2017, pp. 1 through 8.

International Searching Authority, "International Preliminary Report on Patentability," for International Application No. PCT/US2016/029670, dated Oct. 31, 2017, pp. 1 through 7.

United States Patent and Trademark Office Office Action for U.S. Appl. No. 15/139,889, dated Jan. 24, 2019.

(56) References Cited

OTHER PUBLICATIONS

European Examination report, Communication pursuant to Article 94(3), Application No. 16721596.1, dated Jan. 4, 2022.

* cited by examiner

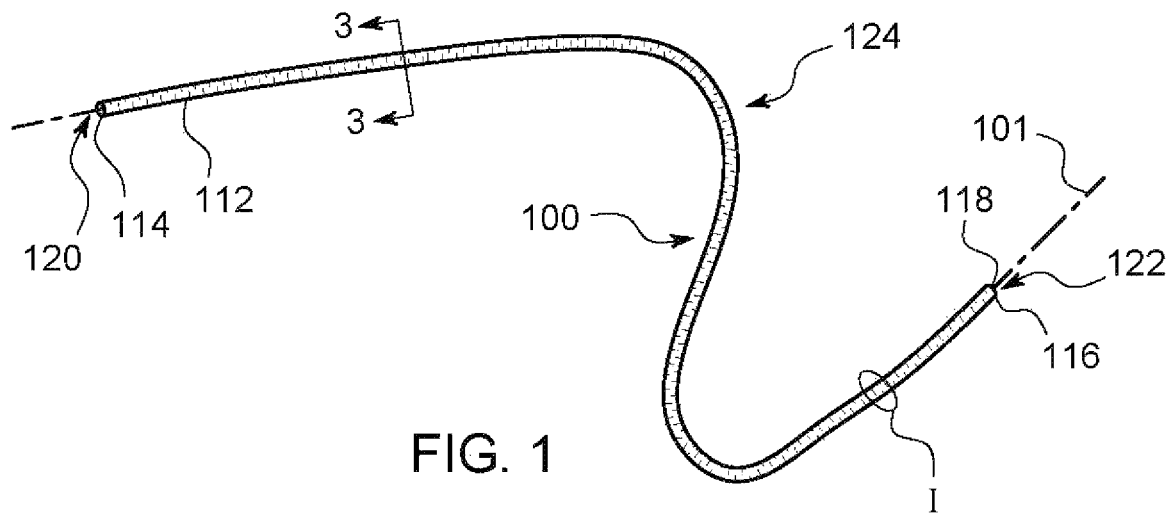
FIG. 1
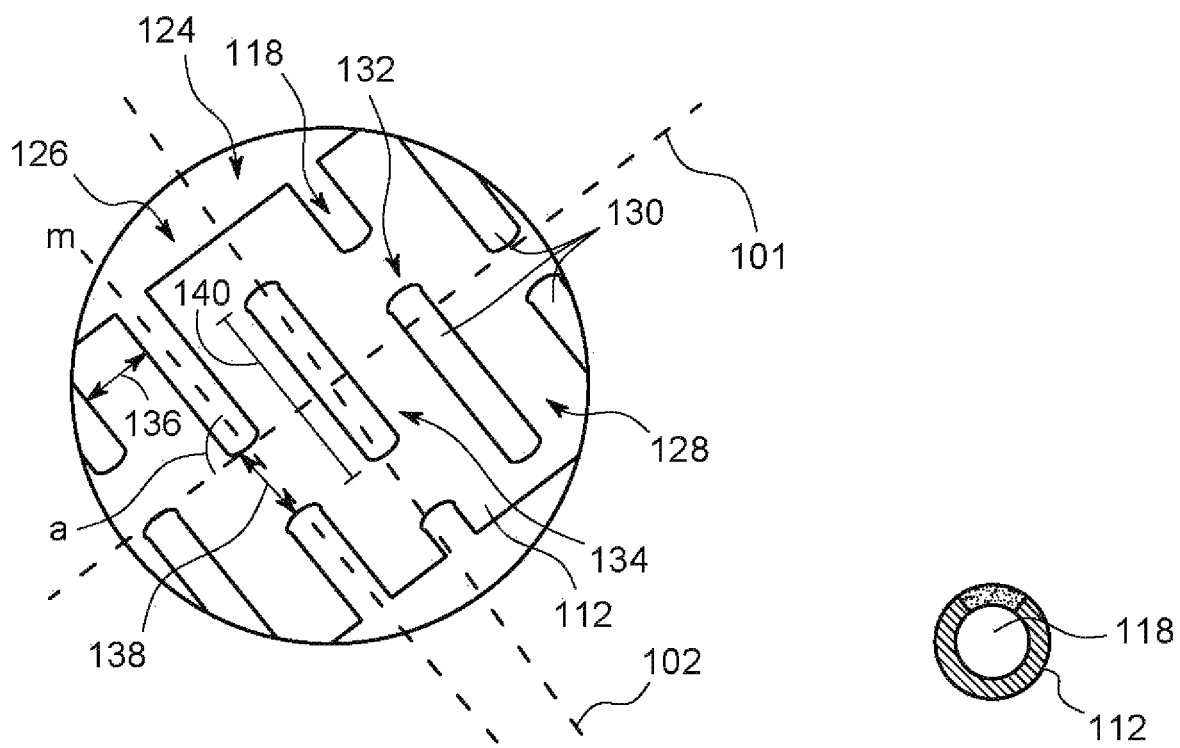
FIG. 2
FIG. 3

MEDICAL CANNULAE, DELIVERY SYSTEMS AND METHODS

CROSS-REFERENCE TO RELATED APPLICATIONS

This application is a continuation of U.S. patent application Ser. No. 15/140,028, filed on Apr. 27, 2016 and issued as U.S. Pat. No. 10,327,933, which claims the benefit of U.S. Provisional Patent Application No. 62/153,814, filed on Apr. 28, 2015. Each of these related applications is incorporated by reference into this disclosure in its entirety.

FIELD

The disclosure relates generally to the field of medical devices. More particularly, the disclosure relates to the fields of cannulae, delivery systems, and methods of making medical devices.

BACKGROUND

Delivery systems for implanting intraluminal medical devices at a point of treatment within a body vessel require both pushability and flexibility. Development of delivery systems and delivery system components that provide these desirable characteristics continues.

BRIEF SUMMARY OF SELECTED EXAMPLES

Several cannulae are described and illustrated herein. An example cannula comprises an elongate tubular member having a circumferential wall extending between a proximal end and a distal end and defining an interior lumen; a pattern of openings extends along a portion of the axial length of the cannula.

Another example cannula comprises an elongate tubular member having a circumferential wall extending between a proximal end and a distal end and defining an interior lumen; a pattern of openings extends along the entire axial length of the cannula.

Another example cannula comprises an elongate tubular member having a circumferential wall extending between a proximal end and a distal end and defining an interior lumen; a pattern of openings extends along an intermediate portion of the axial length of the cannula that is disposed between proximal and distal portions of the cannula that are free of the pattern of openings.

Another example cannula comprises an elongate tubular member having a circumferential wall extending between a proximal end and a distal end and defining an interior lumen; a pattern of openings extends along an intermediate portion of the axial length of the cannula that is disposed between proximal and distal portions of the cannula that are free of the pattern of openings; the proximal portion is longer than the distal portion.

Several delivery systems are described and illustrated herein. An example delivery system comprises a cannula comprising an elongate tubular member having a circumferential wall extending between a proximal end and a distal end and defining an interior lumen; a pattern of openings extending along an intermediate portion of the axial length of the cannula that is disposed between proximal and distal portions of the cannula that are free of the pattern of openings; the proximal portion is longer than the distal portion; an intraluminal medical device disposed on the distal portion of the cannula; and an elongate outer tubular member defining an outer tubular member lumen. The cannula is disposed within the outer tubular member lumen such that the intraluminal medical device is circumferentially disposed about the cannula and within the outer tubular member lumen.

Several methods of making a cannula are described and illustrated herein. An example method of making a cannula comprises identifying a cannula material and a cannula wall thickness that provides a desired global stiffness for said cannula; identifying one or more axial lengths of said cannula along which a localized stiffness, different from the desired global stiffness, is desired; identifying a pattern of openings that will provide the desired localized stiffness when cut into a cannula formed of the cannula material and having the cannula wall thickness; and cutting the pattern of openings into a cannula formed of the cannula material and having the cannula wall thickness at axial positions that correspond to the one or more axial lengths.

Several methods of making a delivery system are described and illustrated herein. An example method of making a delivery system comprises identifying a cannula material and a cannula wall thickness that provides a desired global stiffness for said cannula; identifying one or more axial lengths of said cannula along which a localized stiffness, different from the desired global stiffness, is desired; identifying a pattern of openings that will provide the desired localized stiffness when cut into a cannula formed of the cannula material and having the cannula wall thickness; cutting the pattern of openings into a cannula formed of the cannula material and having the cannula wall thickness at axial positions that correspond to the one or more axial lengths; disposing an intraluminal medical device on a portion of the cannula that is free of the pattern of openings; and inserting the cannula into an elongate tubular member defining a lumen such that the intraluminal medical device is circumferentially disposed about the cannula and within the lumen.

Additional understanding of the inventive cannulae, delivery systems and methods can be obtained by reviewing the description of selected examples, below, with reference to the appended drawings.

BRIEF DESCRIPTION OF THE DRAWINGS

FIG. 1 is a perspective view of an example cannula.

FIG. 2 is a magnified view of area I in FIG. 1.

FIG. 3 is a magnified sectional view of the example cannula illustrated in FIG. 1, taken along line 3-3.

DETAILED DESCRIPTION OF SELECTED EXAMPLES

Figure 4A:
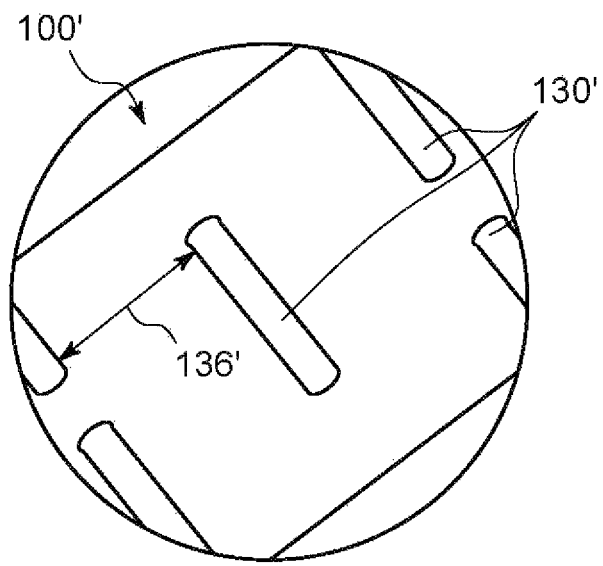
FIG. 4A is a magnified view of a portion of an alternative cannula.

The following detailed description and appended drawings describe and illustrate various examples contemplated by the inventors. The description and drawings serve to enable one skilled in the art to make and use the inventive cannulae and delivery systems, and to practice the inventive methods; they are not intended to limit the scope of the invention or the protection sought in any manner. The invention is capable of being practiced or carried out in various ways; the examples described herein are merely selected examples of these various ways and are not exhaustive. As such, the language used in the description is to be given the broadest possible scope and meaning.

Unless otherwise defined herein, scientific and technical terms used in connection with the invention shall have the meanings that are commonly understood by those of ordinary skill in the art. Further, unless otherwise required by context, singular terms shall include pluralities and plural terms shall include the singular.

As used herein, the term "opening" refers to a passage defined by a member between opposing or substantially opposing surfaces of the member. The term does not require any particular configuration of the passage. Indeed, the term includes rectangular passages, generally rectangular passages, square passages, generally square passages, circular passages, generally circular passages, triangular passages, generally triangular passages, and irregular passages.

As used herein, the term "slit" refers to an opening that has a rectangular or generally rectangular shape when the surfaces between which the passage extends lie on parallel planes.

FIGS. 1, 2 and 3 illustrate a first example cannula 100. The cannula 100 is an elongate tubular member having a circumferential wall 112 extending between a proximal end 114 and a distal end 116. The circumferential wall 112 defines an interior lumen 118. A proximal opening 120 on the proximal end 114 provides access to the interior lumen 118. Similarly, a distal opening 122 on the distal end 116 provides access to the interior lumen 118. A longitudinal axis 101 extends centrally through the lumen. As best illustrated in FIG. 2, each of a plurality of transverse axes, such as transverse axis 102, lies on an individual plane that orthogonally intersects the longitudinal axis 101 at a point along its length.

A pattern of openings 124 extends along a portion of the axial length of the cannula 100. In the illustrated example, the pattern of openings 124 extends along the entire axial length of the cannula 100, extending between the proximal 114 and distal 116 ends. The pattern of openings 124 can extend along any suitable portion of the axial length of the cannula 100, though, and the entire axial length, as in the illustrated cannula 100, is only an example. For a cannula according to a particular example, a skilled artisan will be able to select a suitable portion of the axial length of the cannula along which the pattern of openings is to extend based on various considerations, including any need or desire for axial portions having a greater stiffness than that provided by an axial portion along which the pattern of openings extends. For example, if it is desirable to have an axial portion that has the global stiffness of the cannula material itself, the cannula can be made so that the pattern of openings does not extend along the axial portion for which the global stiffness is desired. Each of FIGS. 5, 6, and 7, described in detail below, illustrates an example cannula in which the pattern of openings does not extend along the entire axial length of the cannula.

As best illustrated in FIG. 2, the pattern of openings 124 comprises a plurality of openings 126 arranged in an interrupted spiral 128 that extends circumferentially along the circumferential wall 112 of the cannula 100. In the illustrated embodiment, each opening 130 of the plurality of openings 126 comprises a slit that extends through the entire wall thickness of the circumferential wall 112 to provide access to the lumen 118 of the cannula 100. The slit of each opening has a generally rectangular shape having a major axis m disposed on a plane that is transverse to the longitudinal axis 101 of the cannula 100. One end 132 of the slit of each opening 130 has a slightly enlarged width, measured along the minor axis of the oblong rectangle of the slit. The overall pattern of openings 124 takes a spiral 128 configuration relative to the longitudinal axis of the cannula 100 because the major axis m of each opening is disposed on a plane that intersects the longitudinal axis 101 of the cannula 100 at a non-orthogonal angle a. Thus opening 134 in FIG. 2, which is illustrated relative to longitudinal axis 101 and transverse axis 102 of cannula 100, is slightly skewed relative to transverse axis 102, as are all other openings 130 in the plurality of openings 124.

The inventors have determined that various parameters of the pattern of openings 124 can be manipulated to achieve a desired stiffness in the cannula 100 along an axial portion of the cannula 100. For example, the distance between revolutions of the spiral, illustrated in FIG. 2 as the gap 136 between openings 130 in immediately adjacent revolutions of the spiral, can be increased or decreased to achieve a desired number of revolutions of the spiral per unit of length of the cannula 100, which, in turn, increases or decreases, respectively, the stiffness of the cannula along the axial portion containing the pattern of openings 124. Stated differently, the pitch of the spiral path along which the openings extend on the cannula can be increased or decreased to achieve a desired stiffness along the axial portion containing the pattern of openings 124. Also, the distance between openings within a revolution of the spiral, illustrated in FIG. 2 as the gap 138 between openings, can be increased or decreased to achieve a desired number of openings in a revolution of the spiral. The major length 140 of the oblong rectangle formed by the openings 130 can be varied as well. Also, the ratio of the major length 140 of the oblong rectangle of the opening to the distance between openings within a revolution of the spiral, i.e., gap 138, can be increased or decreased to achieve a desired number of openings in a revolution of the spiral, which, in turn, increases or decreases, respectively, the stiffness of the cannula along the axial portion containing the pattern of openings 124. The angle a at which a plane containing the major axis m of individual openings 130 intersects the longitudinal axis 101 of the cannula 100 can also be increased or decreased to achieve a desired flexibility.

A skilled artisan will be able to manipulate one or more of these parameters in a cannula according to a particular embodiment to achieve a desired flexibility along the axial portion containing a pattern of openings. Surprisingly, the inventors have determined that a cannula made in this manner retains enough stiffness to effectively serve as the innermost member of a delivery system useful for placing an intraluminal medical device at a point of treatment within a body vessel. While providing a desired degree of local flexibility through manipulation of the parameters described above, such a cannula is able to carry the intraluminal medical device of the delivery system, such as a stent, valve, filter or other expandable intraluminal medical device, and, effectively, serve as a pusher that provides the pushability and/or trackability needed for navigation of the delivery system to an intraluminal point of treatment.

Indeed, while the openings 130 in the illustrated embodiment comprise slits, any suitable opening can be used in a cannula according to a particular embodiment, including openings that provide rectangular passages, openings that provide generally rectangular passages, openings that provide square passages, openings that provide generally square passages, openings that provide circular passages, openings that provide generally circular passages, openings that provide triangular passages, openings that provide generally triangular passages, and openings that provide irregular passages. The inventors have determined, though, that slits are particularly advantageous at least because of the relative ease with which they can be formed in an elongate tubular member and the ease with which they can be aligned along a spiral path on an elongate tubular member.

Figure 4B:
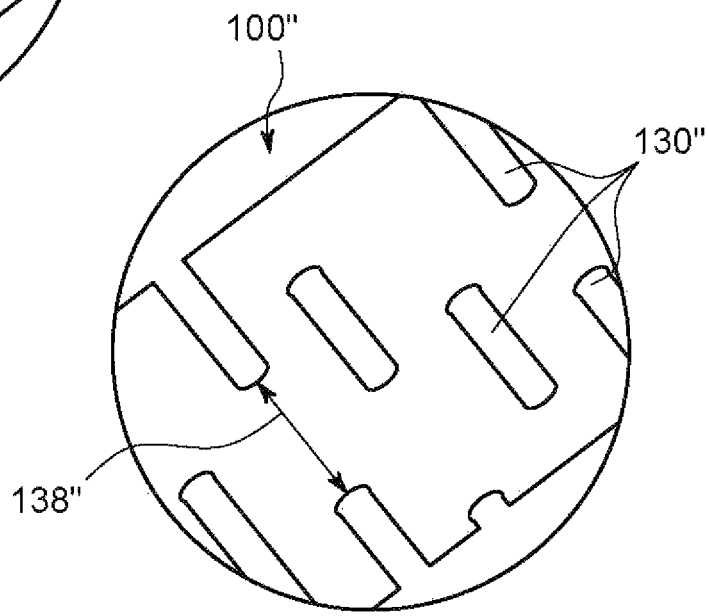
FIG. 4B is a magnified view of a portion of another alternative cannula.
Figure 4C:
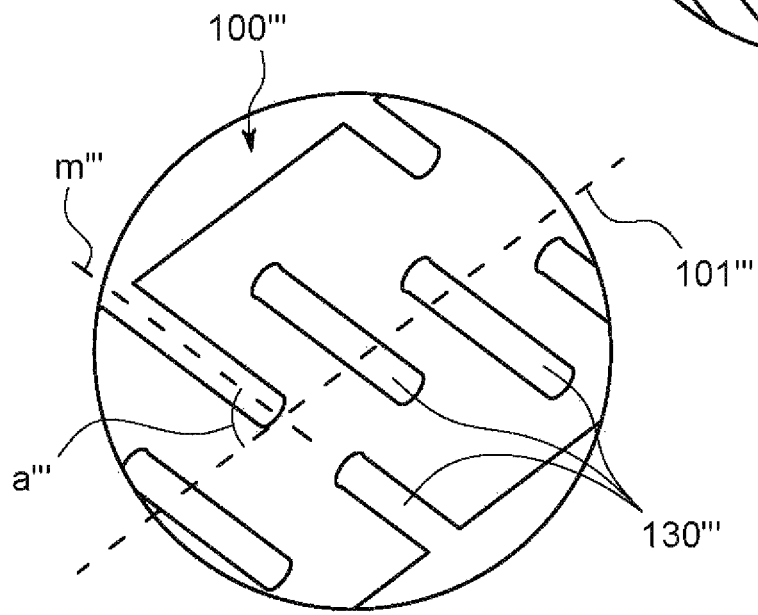
FIG. 4C is a magnified view of a portion of another alternative cannula.

Each of FIGS. 4A, 4B, and 4C illustrates an alternative cannula with wall openings arranged in an alternative pattern achieved by manipulating one or more of the parameters described above. In the cannula 100' illustrated in FIG. 4A, the gap 136' between openings 130' in immediately adjacent revolutions of the spiral is larger than the gap 136 used in cannula 100 illustrated in FIGS. 1 through 3.

The gap between openings in immediately adjacent revolutions of the spiral in a cannula according to a particular embodiment can have any suitable length as measured along the longitudinal axis of the cannula. A skilled artisan will be able to select an appropriate length for this gap for a particular cannula according to various considerations, including the nature of the material from which the cannula is formed and any desired flexibility in the axial length of the cannula along which the pattern of openings that contains the gaps extends. The inventors have determined that a gap the is between about 0.5 and about 40.0 times the axial width of the openings in the pattern of openings is suitable for a cannula intended to be used in an intraluminal medical device delivery system as described herein. The inventors also consider a gap that is between about 1 and about 5 times the axial width of the openings in the pattern of openings to be suitable for a cannula intended to be used in an intraluminal medical device delivery system as described herein. The inventors also consider a gap that is between about 1.5 and about 2.5 times the axial width of the openings in the pattern of openings to be suitable for a cannula intended to be used in an intraluminal medical device delivery system as described herein. The inventors also consider a gap that is about 2 times the axial width of the openings in the pattern of openings to be suitable for a cannula intended to be used in an intraluminal medical device delivery system as described herein.

In the cannula 100" illustrated in FIG. 4B, the gap 138" between openings 130" within a revolution of the spiral is larger than the gap 138 used in cannula 100 illustrated in FIGS. 1 through 3.

The gap between openings within a revolution of the spiral in a cannula according to a particular embodiment can have any suitable length as measured along the major axis of the openings of revolution. A skilled artisan will be able to select an appropriate length for this gap for a particular cannula according to various considerations, including the nature of the material from which the cannula is formed and any desired flexibility in the axial length of the cannula along which the pattern of openings that contains the gaps extends. The inventors have determined that a gap that is between about 0.1 and about 2 times the axial length of the openings in the pattern of openings is suitable for a cannula intended to be used in an intraluminal medical device delivery system as described herein. The inventors consider a gap that is between about 0.25 and about 1.5 times the axial length of the openings in the pattern of openings to be suitable for a cannula intended to be used in an intraluminal medical device delivery system as described herein. The inventors also consider a gap that is between about 0.5 and about 1.25 times the axial length of the openings in the pattern of openings to be suitable for a cannula intended to be used in an intraluminal medical device delivery system as described herein. The inventors also consider a gap that is about 0.5 times the axial length of the openings in the pattern of openings to be suitable for a cannula intended to be used in an intraluminal medical device delivery system as described herein.

In the cannula 100''' illustrated in FIG. 4C, the angle a''' at which each of the planes containing a major axis of an opening 130''' intersects the longitudinal axis 101''' of the cannula 100''' is smaller, or more acute, than the angle a used in cannula 100 illustrated in FIGS. 1 through 3.

The angle at which each of the planes containing a major axis of an opening intersects the longitudinal axis of a cannula according to a particular embodiment can have any suitable measure. A skilled artisan will be able to select an appropriate measure for this angle for a particular cannula according to various considerations, including the nature of the material from which the cannula is formed and any desired flexibility in the axial length of the cannula along which the pattern of openings that contains the angle extends. The inventors have determined that an angle that is between about 5 degrees and about 89 degrees is suitable for a cannula intended to be used in an intraluminal medical device delivery system as described herein. The inventors consider an angle that is between about 45 degrees and about 89 degrees to be suitable for a cannula intended to be used in an intraluminal medical device delivery system as described herein. The inventors also consider an angle that is between about 75 degrees and about 89 degrees to be suitable for a cannula intended to be used in an intraluminal medical device delivery system as described herein. The inventors also consider an angle that is about 85 degrees to be suitable for a cannula intended to be used in an intraluminal medical device delivery system as described herein. Also, it is noted that the angle can be disposed in either direction relative to the cannula. As a result, the openings in the pattern of openings in a cannula according to a particular embodiment can extend toward the proximal end of the cannula or toward the distal end of the cannula.

In the first example cannula 100, the pattern of openings 124 is uniform in that the various parameters described above—the distance between revolutions of the spiral, i.e., gap 136 and, therefore, the pitch of the spiral path along which the openings 130 extend, the distance between openings within a revolution of the spiral, i.e., gap 138, the major length 140 of the oblong rectangle formed by the openings 130, the ratio of the major length 140 of the oblong rectangle of the openings 130 to the distance between openings within a revolution of the spiral, i.e., gap 138, of the openings 130—are uniform throughout the pattern of openings 124. That is, the each of the parameters has a substantially constant value that does not vary within the axial portion of the cannula along which the pattern of openings 124 extends. For some cannula, though, it may be desirable to have one or more of these parameters vary within the axial portion of the cannula along which the pattern of openings 124 extends.

Figure 5:
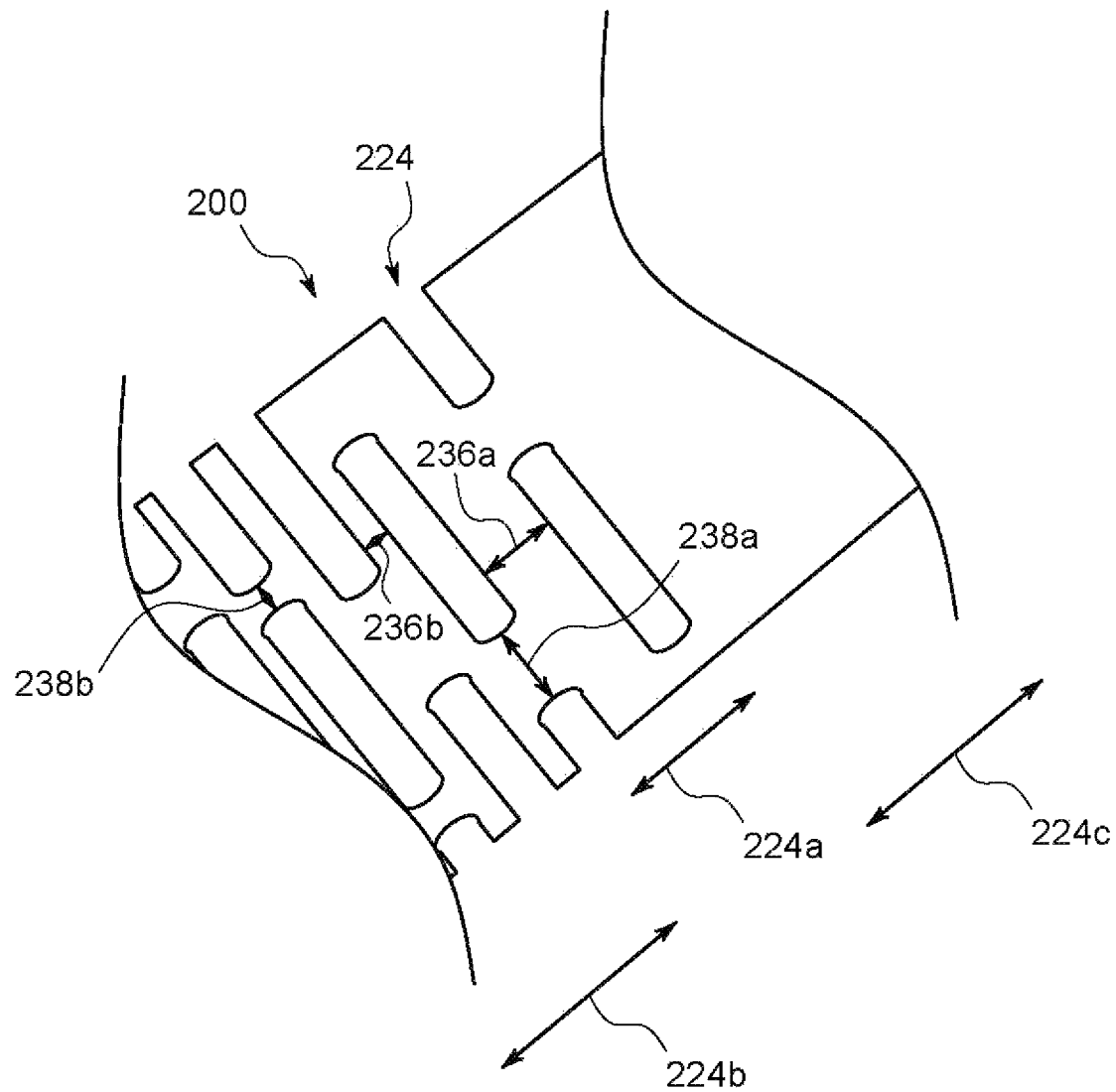
FIG. 5 is a magnified view of a portion of another example cannula.

FIG. 5 illustrates an example cannula 200 in which some of these parameters vary within the axial portion of the cannula 200 along which the pattern of openings 224 extends. For example, an intermediate portion 224a of the pattern of openings includes a first distance between revolutions of the spiral, i.e., gap 236a, and a first distance between openings within a revolution of the spiral, i.e., gap 238a. A proximal portion 224b of the pattern of openings includes a second distance between revolutions of the spiral, i.e., gap 236b, and a second distance between openings within a revolution of the spiral, i.e., gap 238b. Gap 236b is shorter in length that gap 236a. Similarly, gap 238b is shorter in length that gap 238a. A distal portion 224c of the cannula 200 is free of the pattern of openings 224. This construction, where one or more of the parameters described above is varied within a single plurality of openings along an axial portion of a cannula, can be advantageously used in a cannula according to a particular example to provide a stiffness transition between an axial portion of relatively low stiffness, such as proximal portion 224b in cannula 200, to an axial portion of the cannula of relatively high stiffness, such as distal portion 224c of cannula 200, along which the pattern of openings 224 does not extend.

While the pattern of openings can extend along the entire axial length of a cannula, such as in the first example cannula 100, a pattern of openings can extend along any suitable axial length of a cannula according to a particular embodiment. A skilled artisan will be able to select an appropriate axial length for a pattern of openings in a cannula according to a particular embodiment based on various considerations, including whether it is desirable to include any axial portions of the cannula that have a localized stiffness that is greater than the stiffness of the axial portions along which the pattern of openings extends. Each of FIGS. 6, 7, and 8 illustrates a cannula having a pattern of openings that extends along only a portion, or portions, of the entire axial length of the example cannula.

Figure 6:
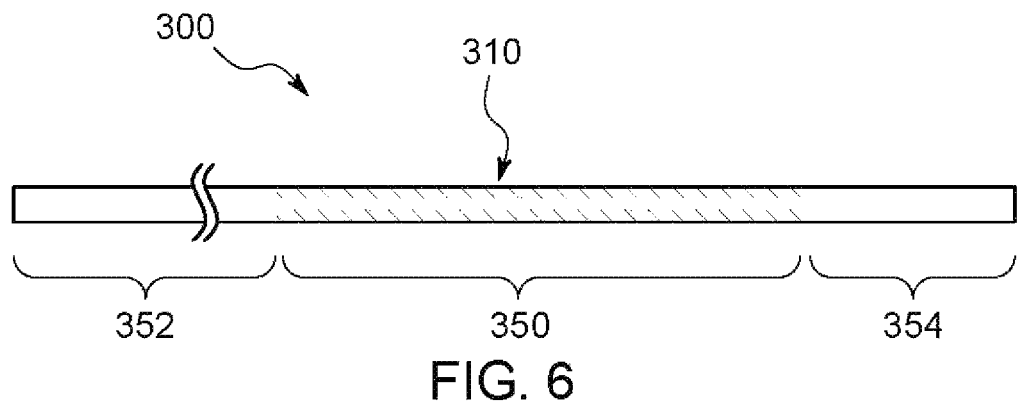
FIG. 6 is a side view, partially broken away, of another example cannula.

The cannula 300 illustrated in FIG. 6 has a pattern of openings 310 that extends along an intermediate portion 350 of the axial length of the cannula 300. The pattern of openings 310 can be any suitable pattern of openings according to an embodiment, including those described above. The intermediate portion 350 extends between a proximal portion 352 and a distal portion 354, each of which is free of the pattern of openings 310 and, indeed, comprises a solid, non-interrupted circumferential wall. This structural configuration is considered advantageous at least because it provides a relatively stiff distal portion 354 that is suitable for carrying an intraluminal medical device when the cannula 300 is included as a component in a delivery system, such as those described below. Furthermore, this configuration provides a relatively stiff proximal portion 352 that facilitates manipulation of the cannula 300, or a delivery system that includes the cannula, by a user.

Each of the intermediate 350, proximal 352 and distal 354 portions can extend along any suitable axial length of the cannula 300, and a skilled artisan will be able to determine suitable axial lengths for each portion in a particular cannula based on various considerations, including the axial length of any intraluminal medical device with which the cannula is intended to be used. Furthermore, the portions can have any suitable relative axial lengths. For example, in the illustrated embodiment, the proximal portion 352 is longer than the distal portion 354. It is noted, though, that an opposite relationship could be used, i.e., the distal portion of a cannula can have a longer axial length than a proximal portion.

Figure 7:
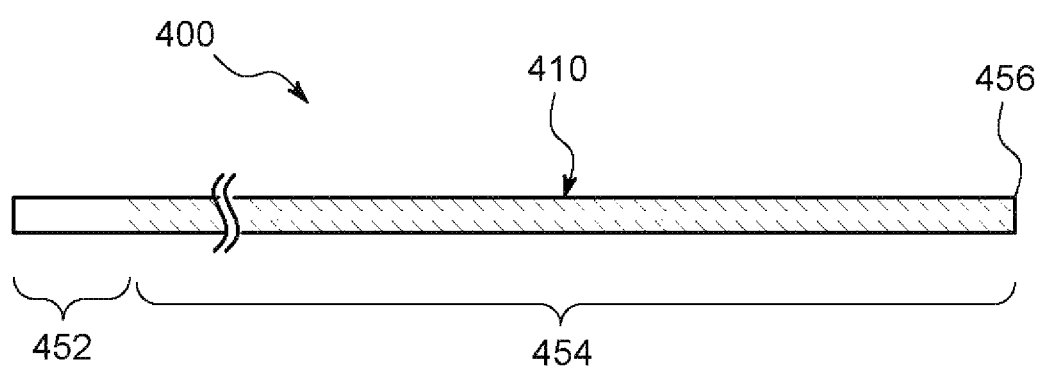
FIG. 7 is a side view, partially broken away, of another example cannula.
Figure 8:
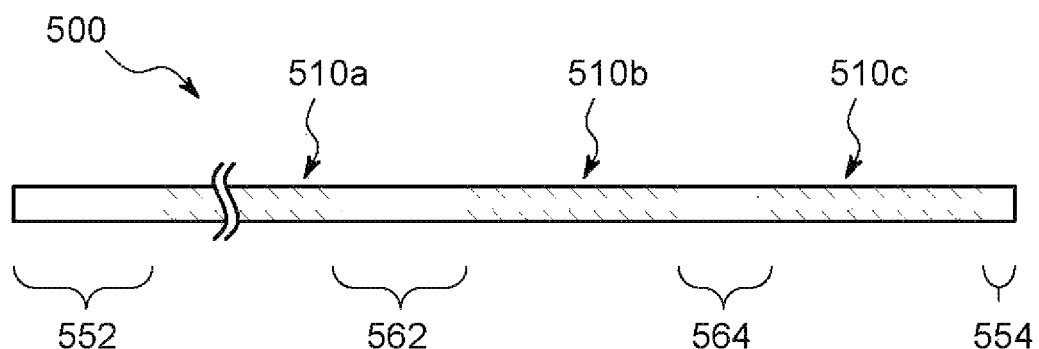
FIG. 8 is a side view, partially broken away, of another example cannula.

The cannula 400 illustrated in FIG. 7 has a pattern of openings 410 that extends along a distal portion 454 of the axial length of the cannula 400. The pattern of openings 410 can be any suitable pattern of openings according to an embodiment, including those described above. The distal portion 454 includes the distal end 456 of the cannula 400. A proximal portion 452 is free of the pattern of openings 410 and, indeed, comprises a solid, non-interrupted circumferential wall. This structural configuration is considered advantageous at least because it provides a relatively flexible distal portion 454 that is suitable for carrying some intraluminal medical devices through tortuous anatomy, such as neurovascular stents. Furthermore, this configuration provides a relatively stiff proximal portion 452 that facilitates manipulation of the cannula 400, or a delivery system that includes the cannula, by a user.

Each of the proximal 452 and distal 454 portions can extend along any suitable axial length of the cannula 400, and a skilled artisan will be able to determine suitable axial lengths for each portion in a particular cannula based on various considerations, including the axial length of any intraluminal medical device with which the cannula is intended to be used. Furthermore, the portions can have any suitable relative axial lengths. For example, in the illustrated embodiment, the proximal portion 452 is shorter than the distal portion 454. It is noted, though, that an opposite relationship could be used, i.e., the distal portion of a cannula can have a longer axial length than a proximal portion.

The cannula 500 illustrated in FIG. 8 has a pattern of openings 510 that comprises distinct sections 510a, 510b, and 510c that are separated from each other by intervening sections 562, 564. The cannula 500 also includes a proximal portion 552 and a distal portion 554, each of which is free of the pattern of openings 510 and, indeed, comprises a solid, non-interrupted circumferential wall. In each of the distinct sections 510a, 510b, 510c, the pattern of openings 510 can be any suitable pattern of openings according to an embodiment, including those described above. Furthermore, the pattern of openings in each of the distinct sections 510a, 510b, 510c can be the same pattern as in the other distinct sections 510a, 510b, 510c. Alternatively, the pattern of openings in each of the distinct sections 510a, 510b, 510c can be different from the pattern of openings in one or two of the other distinct sections 510a, 510b, 510c. Also, each of the distinct sections 510a, 510b, 510c can have any suitable axial length along the cannula 500. In the illustrated embodiment, each of the distinct sections 510a, 510b, 510c extends along an axial length of the cannula 500 that is the same as the axial length along which the other of the distinct sections 510a, 510b, 510c extends along. It is noted, though, that each of the distinct sections 510a, 510b, 510c can extend along an axial length that is different from the axial length along which one or more of the other distinct sections 510a, 510b, 510c extends along. Also, in any given embodiment, any suitable number of distinct sections can be used.

In some embodiments, one or more openings in the pattern of openings that are positioned at specific locations on the cannula are arranged relative to other openings in the pattern of openings such that these openings vary from the interrupted spiral that extends circumferentially along the circumferential wall of the cannula. This structural configuration can be used to provide desired structural characteristics, such as preferential bending and resistance to bending, at distinct locations within the pattern of openings and, indeed, on the cannula itself. This structural arrangement can provide particular desirable characteristics when a particular lengthwise axis that lies on the circumferential surface of a cannula is designated as the specific location for openings that vary from the interrupted spiral that extends along the circumferential wall of the cannula.

Figure 9:
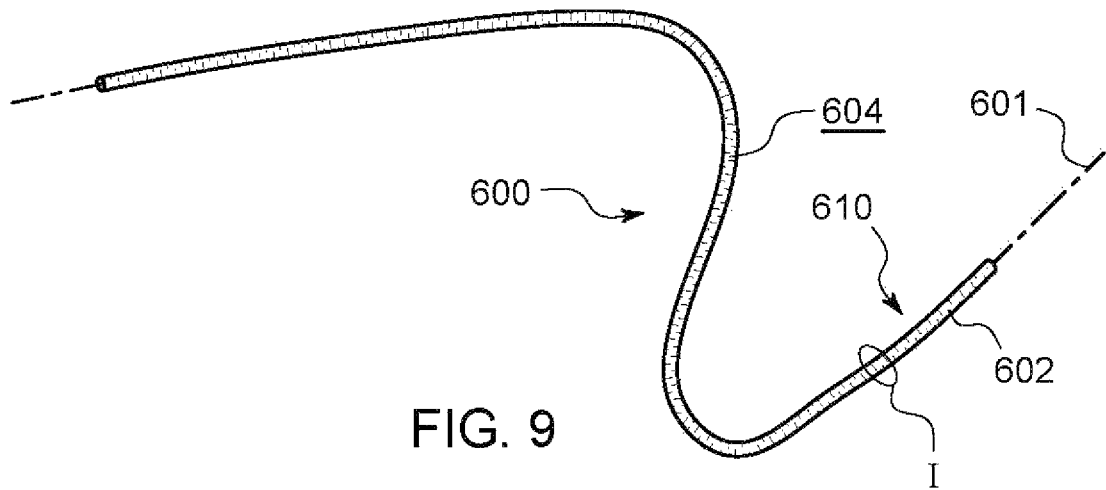
FIG. 9 is a perspective view of another example cannula.
Figure 10:
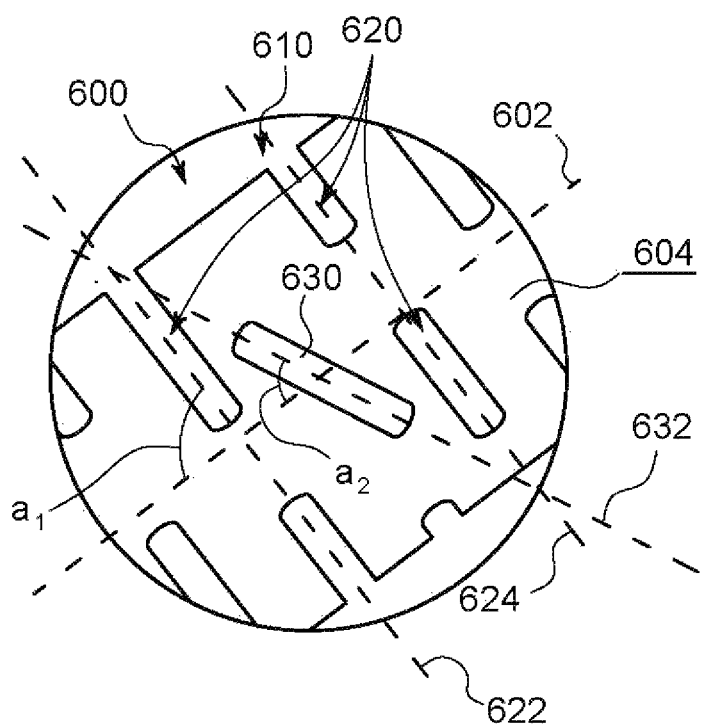
FIG. 10 is a magnified view of area I in FIG. 9.
Figure 11:
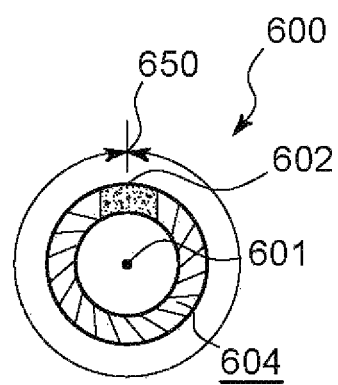
FIG. 11 is a schematic view of a transverse sectional view of the cannula illustrated in FIG. 9, taking within area I.

FIGS. 9, 10 and 11 illustrate an example cannula 600 in which all openings that intersect a particular lengthwise axis 602 that lies on the circumferential surface 604 of the cannula 600 are disposed at an angle relative to the central longitudinal axis 601 of the cannula 600 that is different than the angle at which openings that do not intersect lengthwise axis 602 are disposed relative to the central longitudinal axis 601 of the cannula 600. Thus, as best illustrated in FIG. 10, cannula 600 has a pattern of openings 610 that includes a first set of openings 620 that are disposed on planes 622, 624 that intersect the central longitudinal axis 601 at a first angle $a_1$ and a second set of openings 630 that are disposed on planes, such as plane 632, that intersect the central longitudinal axis 601 at a second angle $a_2$. Circumferentially, as best illustrated in FIG. 11, each of the openings in the second set of openings 630 intersects the particular lengthwise axis 602 and, therefore, intersects a particular circumferential point 650.

In these embodiments, the first $a_1$ and second $a_2$ angles can differ by any suitable amount, and a skilled artisan will be able to select a suitable difference between the angles in a cannula according to a particular embodiment based on various considerations, including any desired degree of stiffness balances against any desired structural characteristic provided by the use of first and second angles, such as preferential bending. Furthermore, both angles can be acute or obtuse, or one angle can be acute and another can be obtuse. The illustrated embodiment, in which both the first $a_1$ and second $a_2$ angles are acute but first $a_1$ angle is greater than the second $a_2$ angle, is one example structural arrangement of many that can be used.

It is noted that, while alternate angles relative to the central longitudinal axis 601 have been described and illustrated, other structural characteristics of the openings that intersect a particular lengthwise axis can differ from other openings in a particular cannula to achieve a desired overall structural characteristics for the cannula. For example, the length, width and even shape and configuration of the intersecting openings can be altered to suitable parameters to achieve a desired characteristic.

Figure 12A:
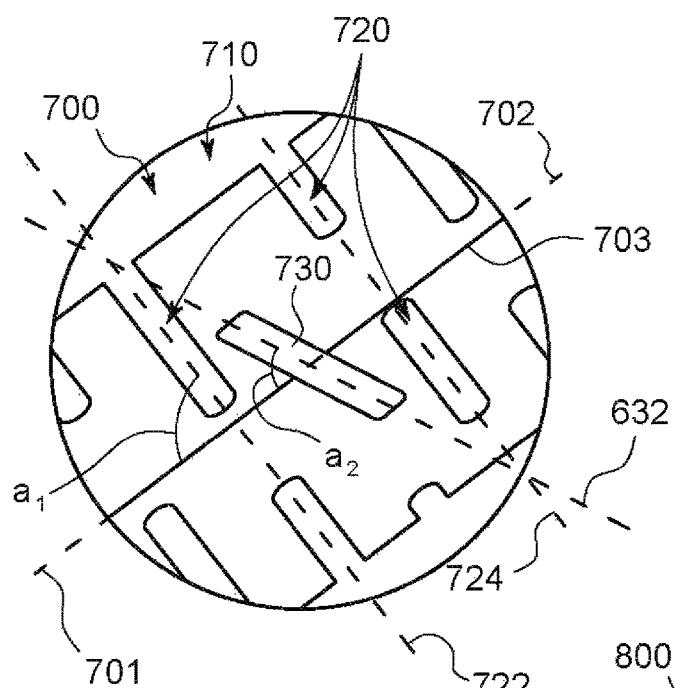
FIG. 12A is a magnified view of another example cannula.
Figure 12B:
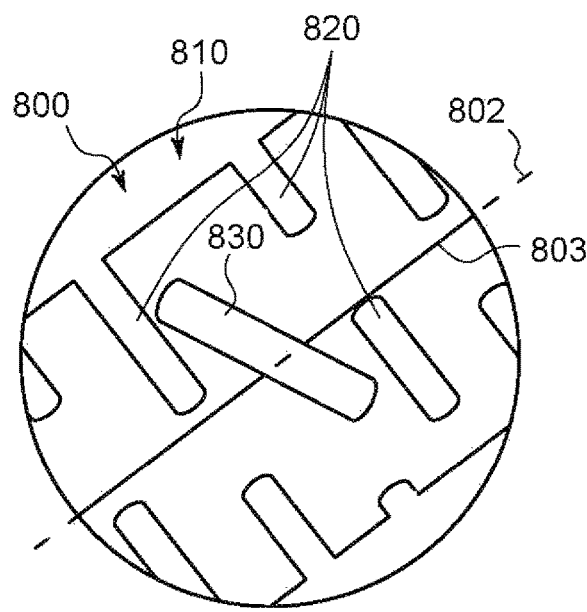
FIG. 12B is a magnified view of another example cannula.
Figure 12C:
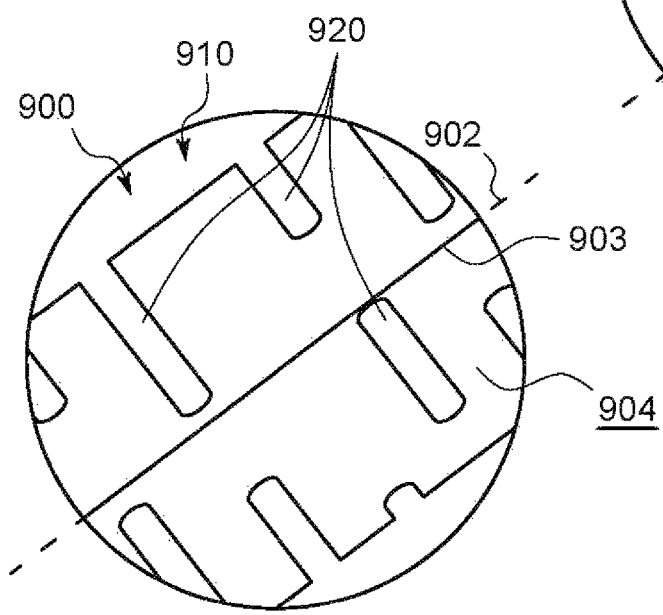
FIG. 12C is a magnified view of another example cannula.

Providing different structural characteristics for openings that intersect a particular longitudinal axis of a cannula, as described above, can provide particularly desirable performance characteristics for a cannula when the axis of intersection lies along a seam in a cannula roll-formed from an initially flat ribbon and joined to form a tube, such as by welding along the seam. FIGS. 12A, 12B, and 12C illustrate example cannulae 700, 800, 900 formed in this manner.

In FIG. 12A, cannula 700 has a pattern of openings 710 that includes a first set of openings 720 that are disposed on planes, such as planes 722, 724, that intersect the central longitudinal axis 701 at a first angle $a_1$ and a second set of openings 730 that are disposed on planes, such as plane 732, that intersect the central longitudinal axis 701 at a second angle $a_2$ that is different than the first angle $a_1$. Each opening in the second set of openings 730 intersects a longitudinal axis 702 that lies along a longitudinal seam 703 in the cannula 700.

In FIG. 12B, cannula 800 has a pattern of openings 810 that includes a first set of openings 820 and a second set of openings 830. Each opening in the second set of openings 830 intersects a longitudinal axis 802 that lies along a longitudinal seam 803 in the cannula 800. In this embodiment, each opening in the second set of openings 830 has a larger width and length than that of each opening in the first set of openings 820. Thus, each opening of the second set of openings 830 has a greater total open area than each opening in the first set of openings 820.

In FIG. 12C, cannula 900 has a pattern of openings 910 that only includes a first set of openings 920. There are no openings in the pattern of openings 910 that intersect a longitudinal axis 902 that lies along a longitudinal seam 903 in the cannula 900. Any opening that would intersect the longitudinal axis 902 and longitudinal seam 903 due to the regular pattern of the pattern of openings 910 extending along a spiral path on the circumferential surface 904 of the cannula has been omitted from the pattern of openings and never formed in the cannula. This structural arrangement may be beneficial in cannulae in which a greater degree of stiffness is desired along a particular lengthwise axis, such as one that lies along a lengthwise seam.

Inclusion of a second pattern of openings within a first pattern of openings can also provide desirable performance characteristics for a cannula. Thus, a cannula can include a second pattern of openings that extends along any suitable axial portion of the axial length along which the first pattern of openings extends. In these embodiments, the second pattern of openings can have the same or different structural properties of the first pattern of openings. For example, the second pattern of openings can have openings of the same size, shape and configuration as those of the first pattern of openings and the second pattern of openings can extend along a spiral path on the cannula having the same pitch as that along which the first pattern of openings extends. Alternatively, the second pattern of openings can have openings having different structural properties of those of the first pattern of openings and/or the openings of the second pattern of openings can extend along a spiral path on the cannula that has a different pitch than that along which the first pattern of openings extends.

Figure 13:
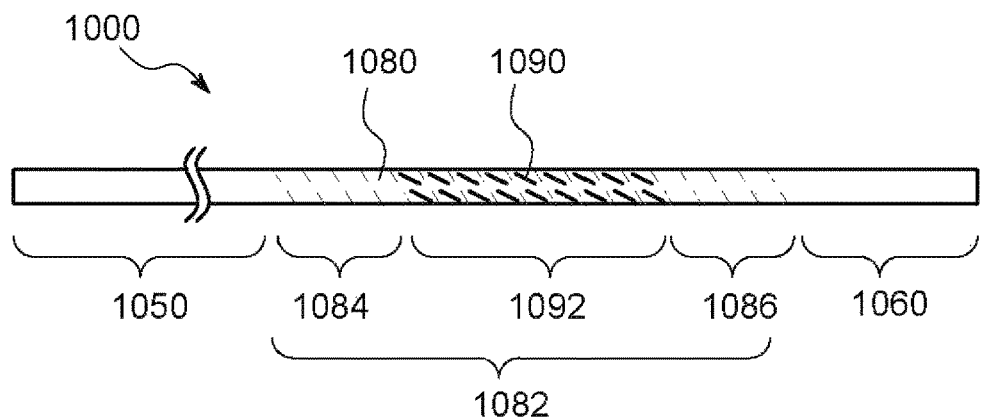
FIG. 13 is a side view, partially broken away, of another example cannula.

FIG. 13 illustrates an example cannula 1000 having first 1080 and second 1090 patterns of openings. The second pattern of openings 1090 extends along an axial portion 1092 of the axial length 1082 along which the first pattern of openings 1080 extends. In the illustrated embodiment, the axial portion 1092 is located within the axial length 1082 such that the axial length 1082 includes proximal 1084 and distal 1086 regions that extend beyond the axial portion 1092. Also, cannula 1000 includes proximal 1050 and distal 1060 axial portions that are free of both patterns of openings 1080, 1090. In the illustrated embodiment, the second pattern of openings 1090 extends along a spiral path on the circumference of the cannula that has a different pitch, a greater pitch, than the pitch of the spiral path along which the first pattern of openings 1080 extends. As noted above, the first 1080 and second 1090 pattern of openings can extend along spiral paths having different pitches, as illustrated, or the same pitches. Also, the openings in the first second 1090 patterns of openings in the illustrated embodiment are longer and wider than the openings in the first pattern of openings. As noted above, the openings of the first 1080 and second 1090 patterns of openings can have different structural characteristics, as illustrated, or can have identical or substantially identical structural characteristics.

A cannula can include one or more additional components. For example, to achieve desired structural and/or performance characteristics for a cannula, an inner member, such as a polymeric shaft or wire member, can be disposed within the lumen defined by a cannula. An outer member, such as an outer sheath or coating, can be disposed circumferentially about a cannula.

Figure 14:
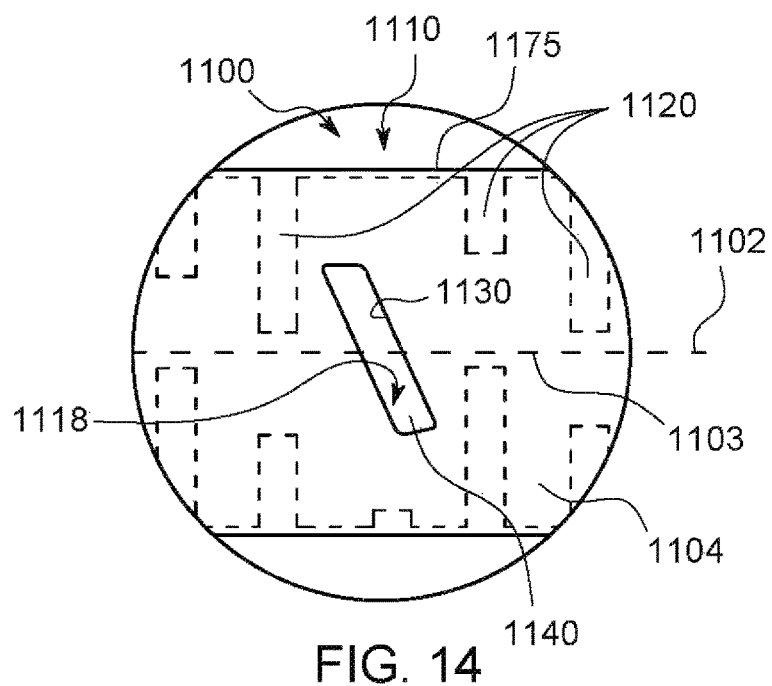
FIG. 14 is a magnified view of another example cannula.
Figure 15:
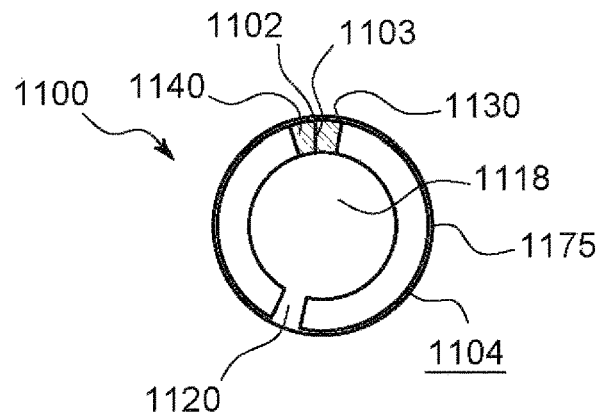
FIG. 15 is a transverse cross-sectional view of the cannula illustrated in FIG. 14.

FIGS. 14 and 15 illustrate an example cannula 1100 around which an outer sheath 1175 has been disposed. In the illustrated embodiment, the outer sheath 1175 comprises a length of tubing that has been disposed circumferentially about the elongate member of the cannula 1100 and shrunk down onto the circumferential surface of the cannula, such as by exposure to heat. Inclusion of an outer sheath in this manner can be advantageous when certain properties are desired for the cannula. For example, the inclusion of an outer Teflon or polyurethane sheath can provide lubriciousness for the cannula, which may be desirable when the cannula is intended to be used as an outer member in a delivery system or on its own.

In these embodiments, the openings of the pattern of openings can be covered by the outer sheath. Alternatively, the outer sheath can be disrupted to provide access to one, at least one, some, a plurality of, or all of the openings of the pattern of openings. This may be desirable when fluid access between the lumen of the cannula and the external environment is desired, such as when fluid flushing from the lumen to the external environment, or vice versa, is desired. In the illustrated embodiment, a first set of openings 1120 of the pattern of openings remain covered by the outer sheath 1175 while the outer sheath 1175 includes disruptions 1130 that provide access to a second set 1140 of openings of the pattern of openings 1110. In this embodiment, each opening of the second set of openings 1140 intersects a longitudinal seam 1103 of the cannula 1100, which lies on a longitudinal axis 1102 on the circumferential surface 1104 of the cannula 1100. The disruptions 1130 in the outer sheath 1175 provide access to the lumen 1118 defined by the cannula 1110. Thus, as best illustrated in FIG. 15, the disruptions 1130 and the points at which fluid access to the lumen 1118 exists, have a known circumferential position on the cannula 1100—the longitudinal seam 1103.

As an alternative to disrupting an outer sheath to provide fluid communication between the lumen defined by the cannula and the external environment, multiple outer sheaths can be disposed circumferentially about the cannula such that they are axially spaced from each other along the length of the cannula, leaving an axial gap between them. By positioning the axial gap or gaps at axial locations that include openings in a pattern of openings disposed on the cannula, the desired fluid communication is established even though the outer sheaths are not disrupted and the openings they extend over are, effectively, blocked.

A cannula according to an example can be made of any suitable material. A skilled artisan will be able to select an appropriate material for a cannula according to a particular example based on various considerations, including any desired overall stiffness and/or flexibility of the cannula and the point of treatment at which the cannula is intended to be used. Metals are considered advantageous for the examples described and illustrated herein, but polymeric, including plastic materials currently considered suitable for use in medical devices, and other materials can be used. Stainless steel is considered particularly advantageous for the example cannulae described and illustrated herein at least because of its well-characterized nature, acceptance as a material used in medical devices temporarily placed within body lumens, and ready availability. Examples of other metals considered suitable for use in cannulae according to particular examples include cobalt-chrome and shape memory alloys, such as nickel-titanium alloys. Examples of polymeric materials considered suitable for use in cannulae according to particular examples include polyamide materials, such as nylon, and other polymeric materials. A cannula can include multiple materials, too, if desired. For example, an axial length of one material can be joined to an axial length of another material to create a cannula. The pattern of openings in such a cannula can be disposed on any suitable axial portion of the cannula, such as an axial portion comprising only the first material, an axial portion comprising only the second material, or an axial portion comprising both the first and the second material.

It is noted that a cannula according to a particular example can have a lumen of any suitable diameter and that the dimensions of the lumen of the cannulae described and illustrated herein are illustrative only. A skilled artisan will be able to select an appropriate lumen size for a cannula according to a particular example based on various considerations, including the dimensions of the lumen of the body vessel within which the cannula and/or delivery system is intended to be used.

It is noted that a cannula according to a particular example can have a circumferential wall of any suitable wall thickness and that the wall thicknesses of the circumferential wall of the cannulae described and illustrated herein are illustrative only. A skilled artisan will be able to select an appropriate wall thickness for a cannula according to a particular embodiment based on various considerations, including any desired overall stiffness of the cannula. Indeed, the inventors have determined that a wall thickness can be selected when making a cannula according to a particular example that provides a desired stiffness to any axial portions of the cannula not having a pattern of openings disposed on the portion of the circumferential wall within that particular axial portion. As described in detail below, combining a selected wall thickness with one or more selected patterns of openings along the axial length of a cannula allows a user to make a cannula with desired global and local stiffnesses.

The cannulae can be used as a component of a delivery system useful for delivering an intraluminal medical device to a point of treatment within a lumen of a body vessel. Indeed, structural characteristics of the cannulae make the cannulae useful as various components of a delivery system. For example, the cannulae can be used as an inner core member in a delivery system, as a pusher in a delivery system, and/or as an outer tubular member of a delivery system. When used as one or more of these components in a delivery system, the desirable stiffness properties of the cannulae provide delivery systems that are particularly well suited for delivering a variety of intraluminal medical devices to points of treatment within various body vessels. For example, delivery systems that include example cannulae are expected to be well-suited for delivery of prosthetic venous valves, stents, filters, occluders, neurovascular stents and other intraluminal medical devices.

Inclusion of a cannula as an inner core member in a delivery system may be advantageous where an intended point of treatment and/or navigation route makes localized flexibility desirable. In these embodiments, an intraluminal medical device can be disposed circumferentially about, and carried by, the cannula, which is then surrounded by an outer elongate tubular member, such as a conventional delivery system sheath.

Figure 16:
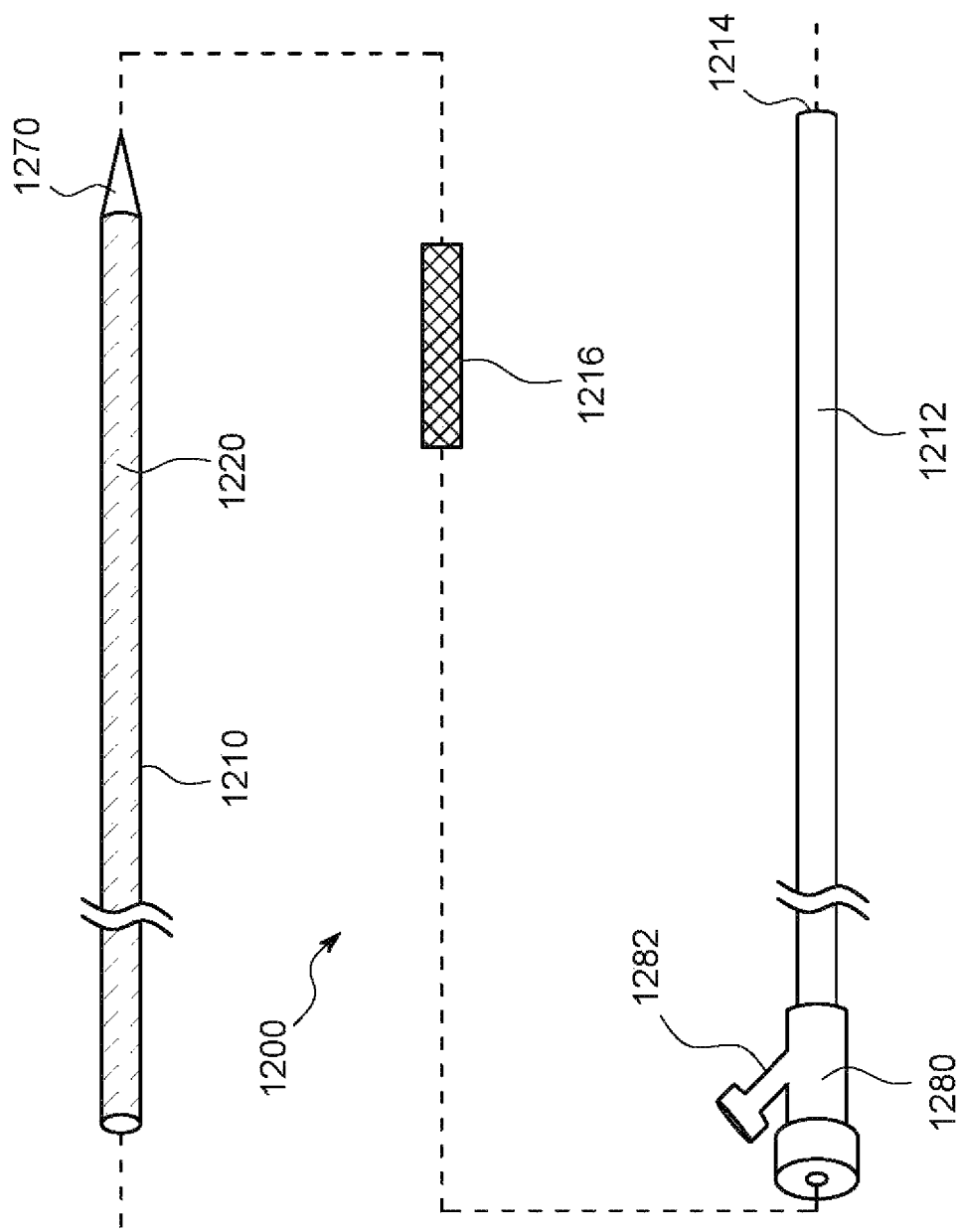
FIG. 16 is an exploded view of an example delivery system.

FIG. 16 illustrates a first example delivery system 1200 in which a cannula according to an embodiment is included as an inner core member. The delivery system 1200 includes a cannula 1210 according to an embodiment disposed within the lumen 1214 defined by an outer tubular member 1212. An intraluminal medical device 1216 is circumferentially disposed around the cannula 1210 and within the lumen 1214 of the outer tubular member 1212.

The cannula 1210 can comprise any suitable cannula according to an embodiment and a skilled artisan will be able to select a suitable cannula for inclusion in a particular delivery system based on various considerations, including the nature, size and configuration of the intraluminal medical device 1216 and any desired local and/or global flexibility and/or stiffness properties for the delivery system 1200. In the illustrated delivery system 1200, a cannula 1210 having a pattern of openings 1220 that extends along the entire axial length of the cannula 1210 is included in the delivery system 1200. This is considered particularly advantageous for delivery systems for which overall flexibility is the primary desired characteristic.

The intraluminal medical device 1216 can comprise any suitable intraluminal medical device. The delivery systems are particularly well-suited, however, for use with self-expandable medical devices, including stents, valves, such as venous valve and cardiac valves, filters, occluders, and other intraluminal medical devices.

Additional components can be attached to the cannula 1210 using conventional approaches. For example, in the illustrated embodiment, a conical distal tip 1270 has been disposed on and secured to the distal end of the cannula 1210. Similarly, additional components can be attached to the elongate tubular member 1214 using conventional approaches. For example, in the illustrated embodiment, a hub 1280 providing a side-arm connector 1282 is disposed on and secured to the proximal end of the elongate tubular member 1212.

It is noted that the cannula 1210 provides desirable flexibility and pushability characteristics for the delivery system 1200 such that additional components, such as a pusher, are not required for its use. Thus, the delivery system can consist only of a cannula according to an embodiment, such as cannula 1210, an elongate tubular member 1212, and an intraluminal medical device 1216. If desired or necessary, the delivery system 1200 can be advanced over a previously-placed wireguide (not shown) for conventional navigation purposes.

Figure 17:
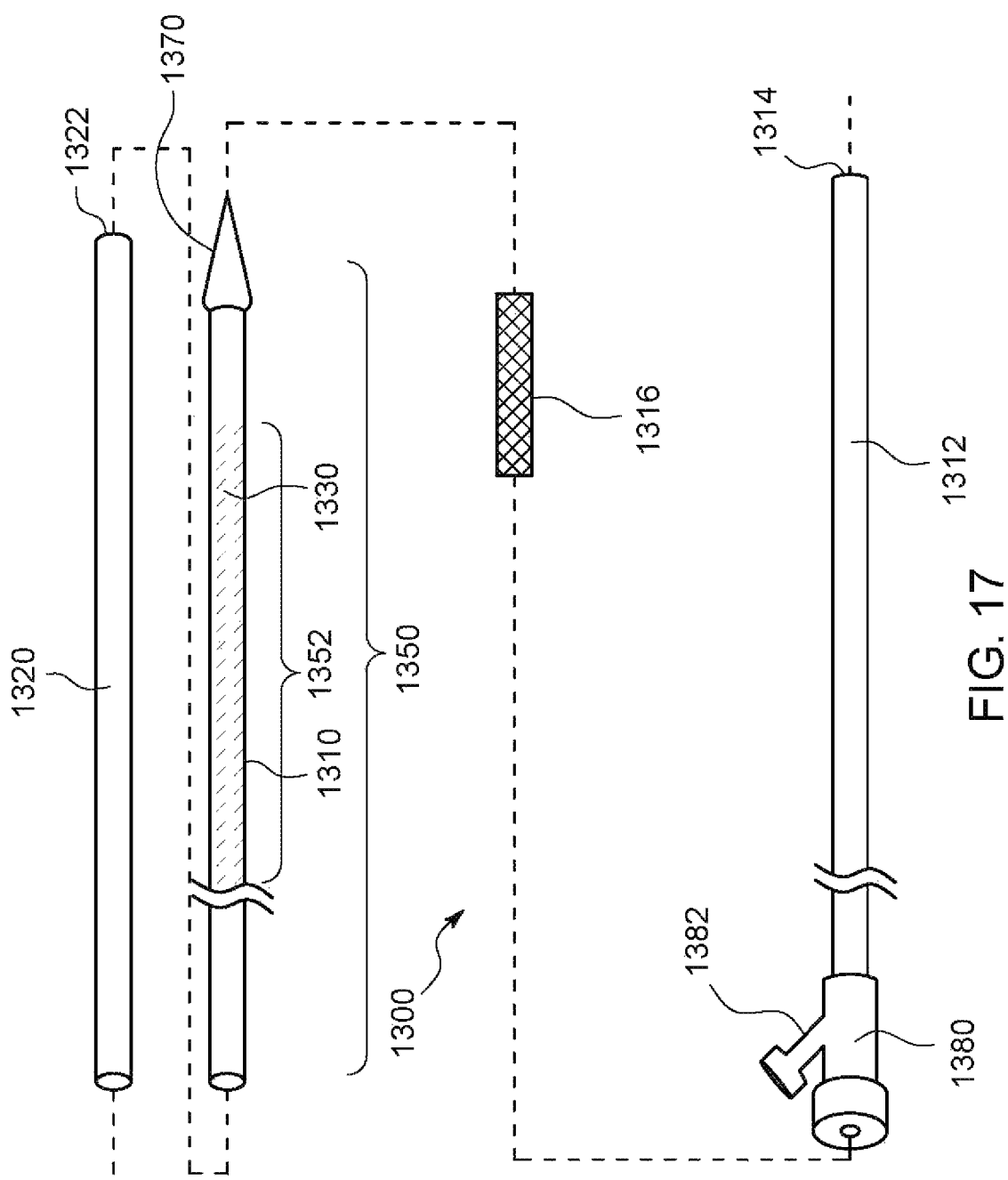
FIG. 17 is an exploded view of another example delivery system.

FIG. 17 illustrates a second example delivery system 1300 in which a cannula according to an embodiment is included as an inner core member. Delivery system 1300 is similar to delivery system 1200 described above and illustrated in FIG. 16, except as detailed below. Thus, delivery system 1300 includes a cannula 1310 according to an embodiment disposed within the lumen 1314 defined by an outer tubular member 1312. An intraluminal medical device 1316 is circumferentially disposed around the cannula 1310 and within the lumen 1314 of the outer tubular member 1312. An elongate double-tapered distal tip 1370 has been disposed on and secured to the distal end of the cannula 1310. A hub 1380 providing a side-arm connector 1382 is disposed on and secured to the proximal end of the elongate tubular member 1312.

The delivery system 1300 also includes tubular pusher 1320 that is slidably disposed over the cannula 1310. During use, the tubular pusher 1320 can be axially advanced over the cannula 1310 toward the intraluminal medical device 1316 until the distal end 1322 of the tubular pusher 1320 abuts or otherwise engages the proximal end of the intraluminal medical device 1316. At that point, the tubular pusher 1320 can continue to be distally advanced, thereby forcing distal advancement of the intraluminal medical device 1316 until it exits the lumen 1314 defined by the outer tubular member 1312. Alternatively, the outer tubular member 1312 can be proximally withdrawn while the position of the tubular pusher 1320 is maintained until the intraluminal medical device 1316 exits the lumen 1314 defined by the outer tubular member 1312.

The cannula 1310 can comprise any suitable cannula according to an embodiment and a skilled artisan will be able to select a suitable cannula for inclusion in a particular delivery system based on various considerations, including the nature, size and configuration of the intraluminal medical device 1316 and any desired local and/or global flexibility and/or stiffness properties for the delivery system 1300. In the illustrated embodiment, the cannula 1310 is similar to the cannula 300 illustrated in FIG. 6. Thus, the cannula 1310 has a pattern of openings 1330 that extends along an intermediate portion 1352 of the axial length 1350 of the cannula 1310. The pattern of openings 1310 can be any suitable pattern of openings according to an embodiment, including those described above. The intermediate portion 1352 extends between a proximal portion 1354 and a distal portion 1356, each of which is free of the pattern of openings 1300 and, indeed, comprises a solid, non-interrupted circumferential wall. This structural configuration is considered advantageous at least because it provides a relatively stiff distal portion 1356 that is suitable for carrying the intraluminal medical device 1316 and provides a relatively stiff proximal portion 1354 that facilitates manipulation of the delivery system 1300 during use. This arrangement is considered advantageous for use with low profile intraluminal medical devices, such as stents.

Figure 18:
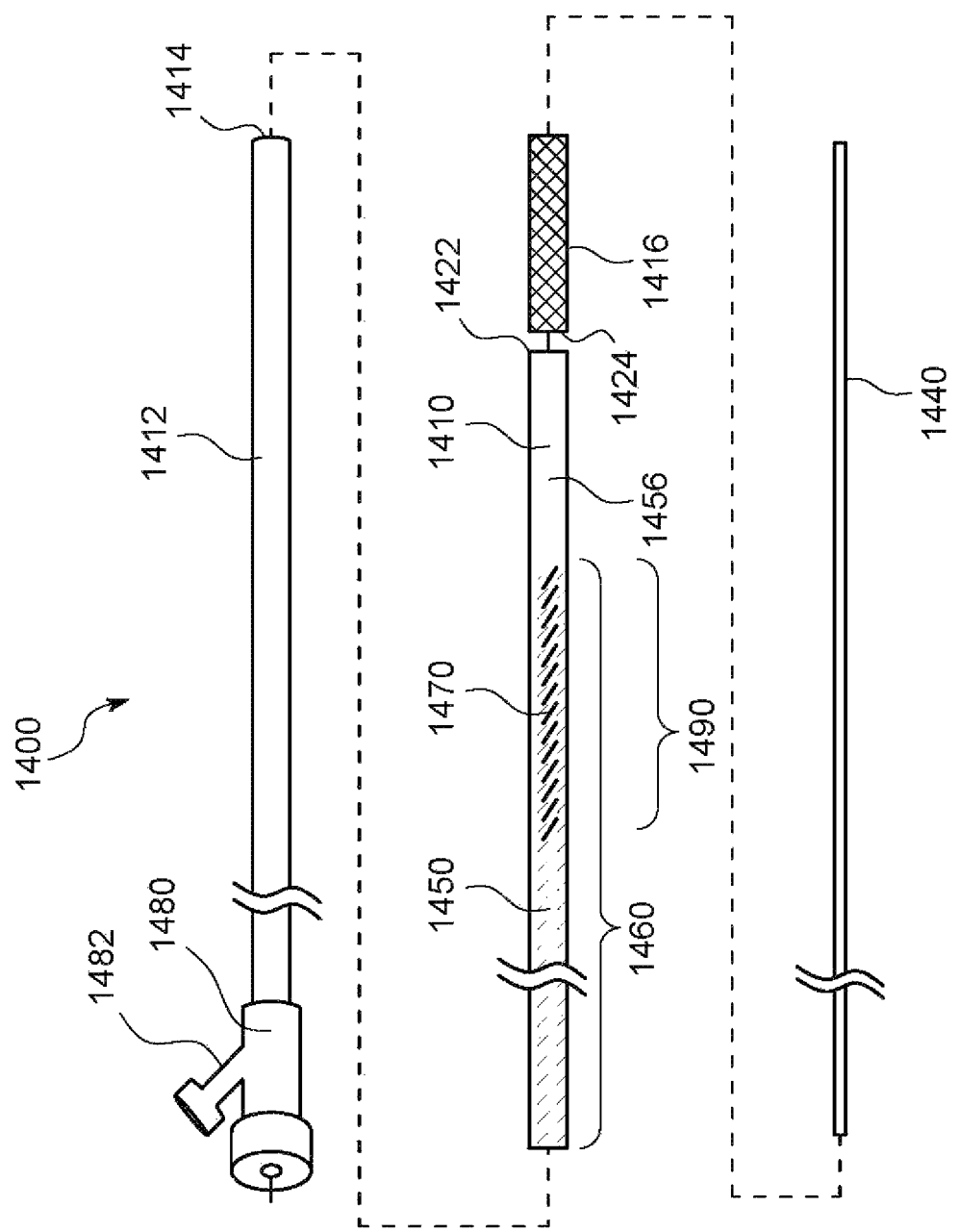
FIG. 18 is an exploded view of another example delivery system.

FIG. 18 illustrates an example delivery system 1400 in which a cannula according to an embodiment is included as a pusher and, along with an intraluminal medical device, is disposed circumferentially about an inner member. In this embodiment, delivery system 1400 includes a cannula 1410 according to an embodiment disposed within the lumen 1414 defined by an outer tubular member 1412. An intraluminal medical device 1416 is circumferentially disposed within the lumen 1414 of the outer tubular member 1412 and distal to the cannula 1410. In this embodiment, the intraluminal medical device is not disposed about the cannula 1410 in the fully assembled delivery system 1400. A hub 1480 providing a side-arm connector 1482 is disposed on and secured to the proximal end of the elongate tubular member 1412.

In this embodiment, the cannula 1410 and intraluminal medical device 1416 are each circumferentially disposed about an inner core member 1440, such as a solid core member, a lumen-defining member, or a wire. As such, the cannula 1410 is positioned for use as a pusher on the intraluminal medical device 1416. Thus, during use, the cannula 1410 can be axially advanced over the inner core member 1440 toward the intraluminal medical device 1416 until the distal end 1422 of the cannula 1410 abuts or otherwise engages the proximal end 1424 of the intraluminal medical device 1416. At that point, the cannula 1410 can continue to be distally advanced, thereby forcing distal advancement of the intraluminal medical device 1416 until it exits the lumen 1414 defined by the outer tubular member 1412. Alternatively, the outer tubular member 1412 can be proximally withdrawn while the position of the cannula 1410 is maintained until the intraluminal medical device 1416 exits the lumen 1414 defined by the outer tubular member 1412.

The cannula 1410 can comprise any suitable cannula according to an embodiment and a skilled artisan will be able to select a suitable cannula for inclusion in a particular delivery system based on various considerations, including the nature, size and configuration of the intraluminal medical device 1416 and any desired local and/or global flexibility and/or stiffness properties for the delivery system 1400. In the illustrated embodiment, the cannula 1410 is similar to the cannula 1000 illustrated in FIG. 13. Thus, the cannula 1410 has a first pattern of openings 1450 that extends along a first axial length 1460 of the cannula 1410 and a second pattern of openings 1470 that extends along a second axial length 1470 of the cannula 1410. The second axial length 1460 is a portion of the first axial length 1480, which provides an axial length 1490 of the cannula 1410 along which both the first 1450 and second 1470 pattern of openings extend. In the illustrated embodiment, the second pattern of openings 1470 is a plurality of openings that extends linearly along only a single side of the intermediate axial portion of the cannula 1410. Also, the openings of the second pattern of openings 1470 are interspersed with the openings of the first pattern of openings 1450. This structural configuration is considered advantageous at least because it provides a relatively stiff distal portion 1456 that is suitable for contacting and pushing the intraluminal medical device 1416 and provides an axial length 1490 having enhanced flexibility.

Figure 19:
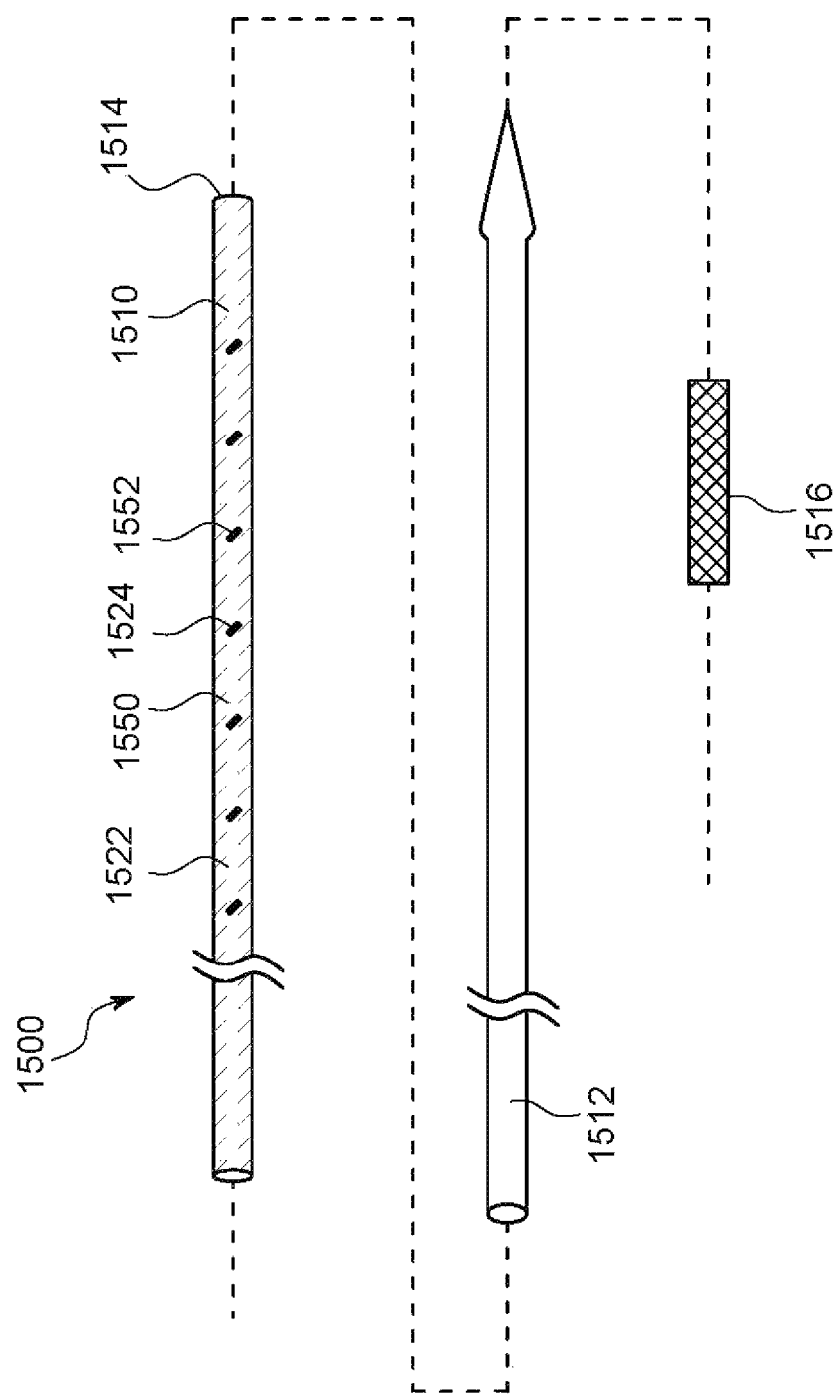
FIG. 19 is an exploded view of another example delivery system.

FIG. 19 illustrates an example delivery system 1500 in which a cannula 1510 according to an embodiment is included as an outer tubular member that is disposed circumferentially about inner components of the delivery system. That is, an inner member, such as a dilator 1512 on which an intraluminal medical device 1516 is circumferentially disposed, is disposed within a lumen 1514 defined by the cannula 1510. In this embodiment, the cannula 1510 includes a full-length outer sheath 1550 disposed over and secured to the cannula 1510. The cannula 1510 includes a pattern of openings 1520. A first set of openings 1522 of the pattern of openings 1520 are covered by the outer sheath and a second set of openings 1524 are adjacent disruptions 1552 in the outer sheath 1550 that establish communication between the external environment and the lumen 1514 defined by the cannula 1510. This structural configuration is considered advantageous at least because it provides fluid communication channels that can be used for flushing the delivery system 1500 before, during or after deployment of the intraluminal medical device 1516 at a point of treatment.

Figures 20, 21:
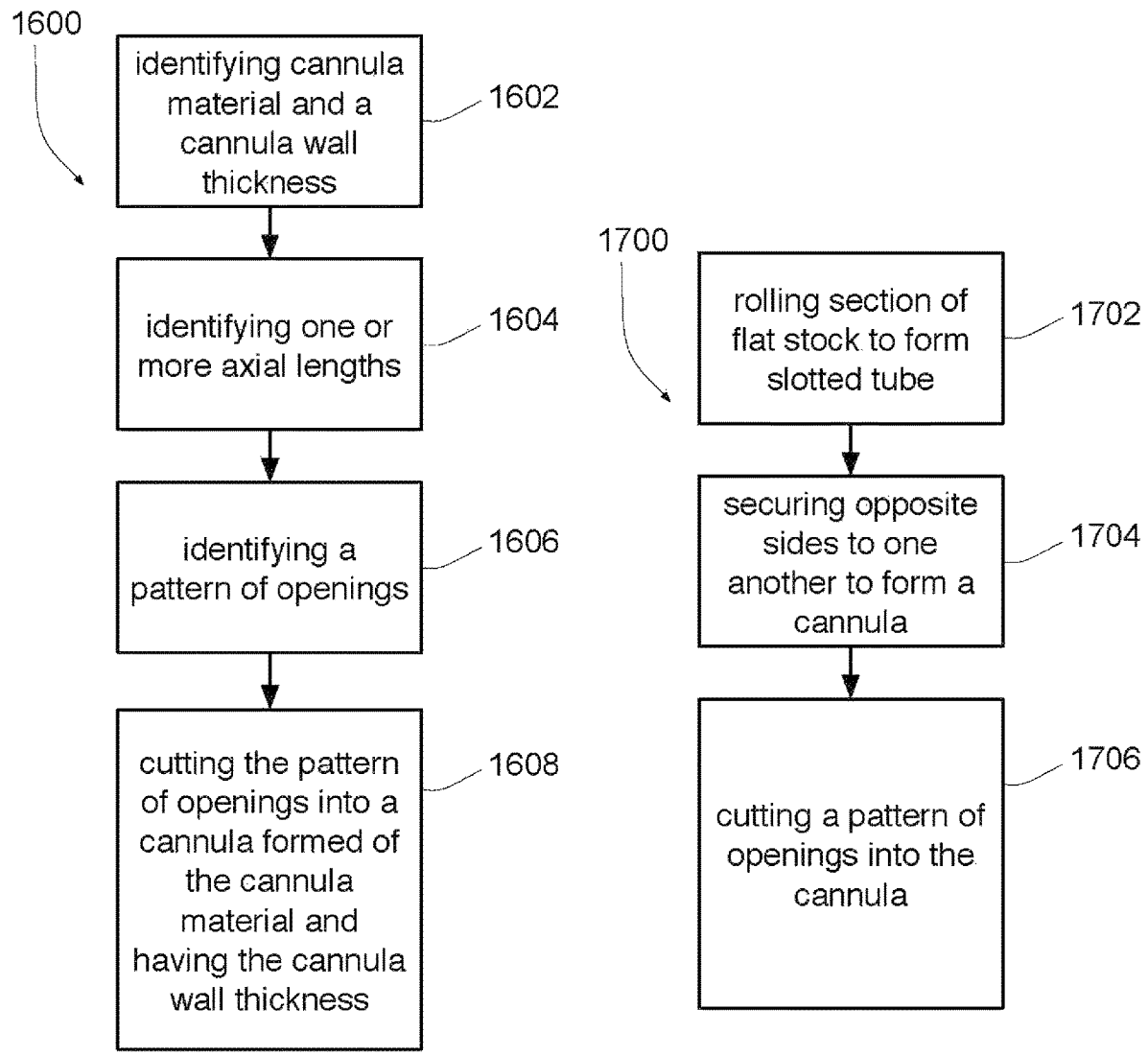
FIG. 20 is a flowchart representation of an example method of making a cannula.
FIG. 21 is a flowchart representation of an example method of making a cannula.

FIG. 20 illustrates an example method 1600 of making a cannula. A first step 1602 comprises identifying a cannula material and a cannula wall thickness that provides a desired global stiffness for said cannula. Another step 1604 comprises identifying one or more axial lengths of said cannula along which a localized stiffness, different from the desired global stiffness, is desired. Another step 1606 comprises identifying a pattern of openings that will provide the desired localized stiffness when cut into a cannula formed of the cannula material and having the cannula wall thickness. Another step 1608 comprises cutting the pattern of openings into a cannula formed of the cannula material and having the cannula wall thickness at axial positions that correspond to the one or more axial lengths.

FIG. 21 illustrates another example method 1700 of making a cannula. A first step 1702 comprises rolling a section of flat stock to form a slotted tube in which opposite sides of the flat stock are disposed opposite one another relative to a slot in the slotted tube. Another step 1704 comprises securing the opposite sides to one another, to close, substantially close, or partially close the slot to form a cannula. Another step 1706 comprises cutting a pattern of openings into the cannula.

The step 1702 of rolling a sheet of flat stock can be performed in any suitable manner and using any suitable technique and/or equipment. The step 1704 of securing the opposite sides to one another can be performed in any suitable manner and using any suitable technique and/or equipment. Welding the sides to each other and adhering the sides to each other are examples of suitable techniques that can be used. The step 1706 of cutting a pattern of openings into the cannula can be performed in any suitable manner and using any suitable technique and/or equipment. Furthermore, any suitable pattern of openings can be made during performance of this step, including the various patterns of openings described and illustrated herein. In an alternative method an initial step of cutting a pattern of openings into the section of flat stock is included. In another alternative method, the step 1706 of cutting a pattern of openings into the cannula is eliminated and an initial step of cutting a pattern of openings into the section of flat stock is included.

Figure 22:
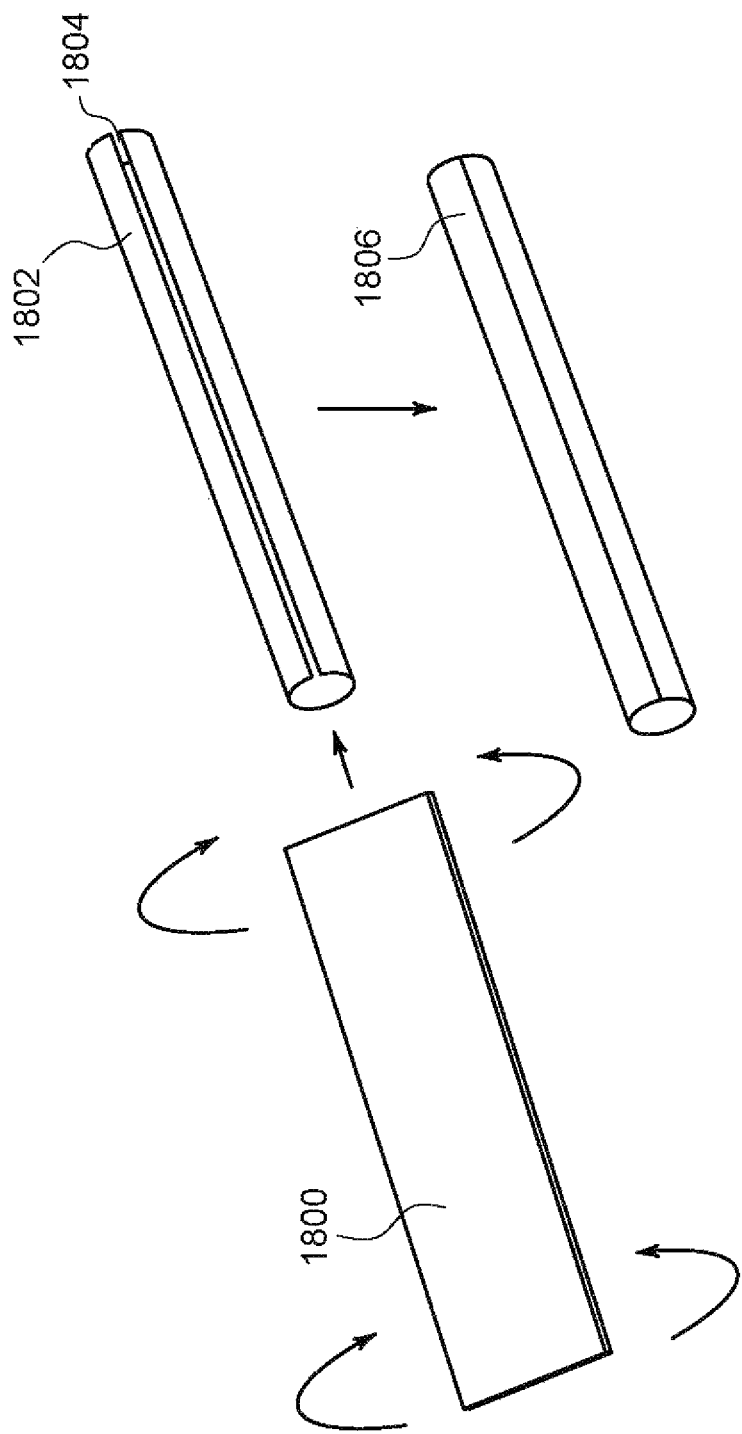
FIG. 22 is a schematic representation of a transformation of matter that occurs with performance of the method illustrated in FIG. 21.

FIG. 22 is a schematic illustration of a transformation of matter that occurs with performance of steps of the method illustrated in FIG. 21. A section of flat stock, such as ribbon 1800, is rolled to form slotted tube 1802 having longitudinal slot 1804. A longitudinal weld join 1806 is formed to close longitudinal slot and to form cannula 1808. A pattern of openings can then be cut into the cannula 1806 using any suitable technique and/or process, such as laser cutting followed by post-processing to remove any slag created as a result of the cutting. Alternatively, a suitable laser capable of cutting the pattern of openings entirely by vaporization can be used to avoid the need for removal of slag in post-processing.

Figure 23:
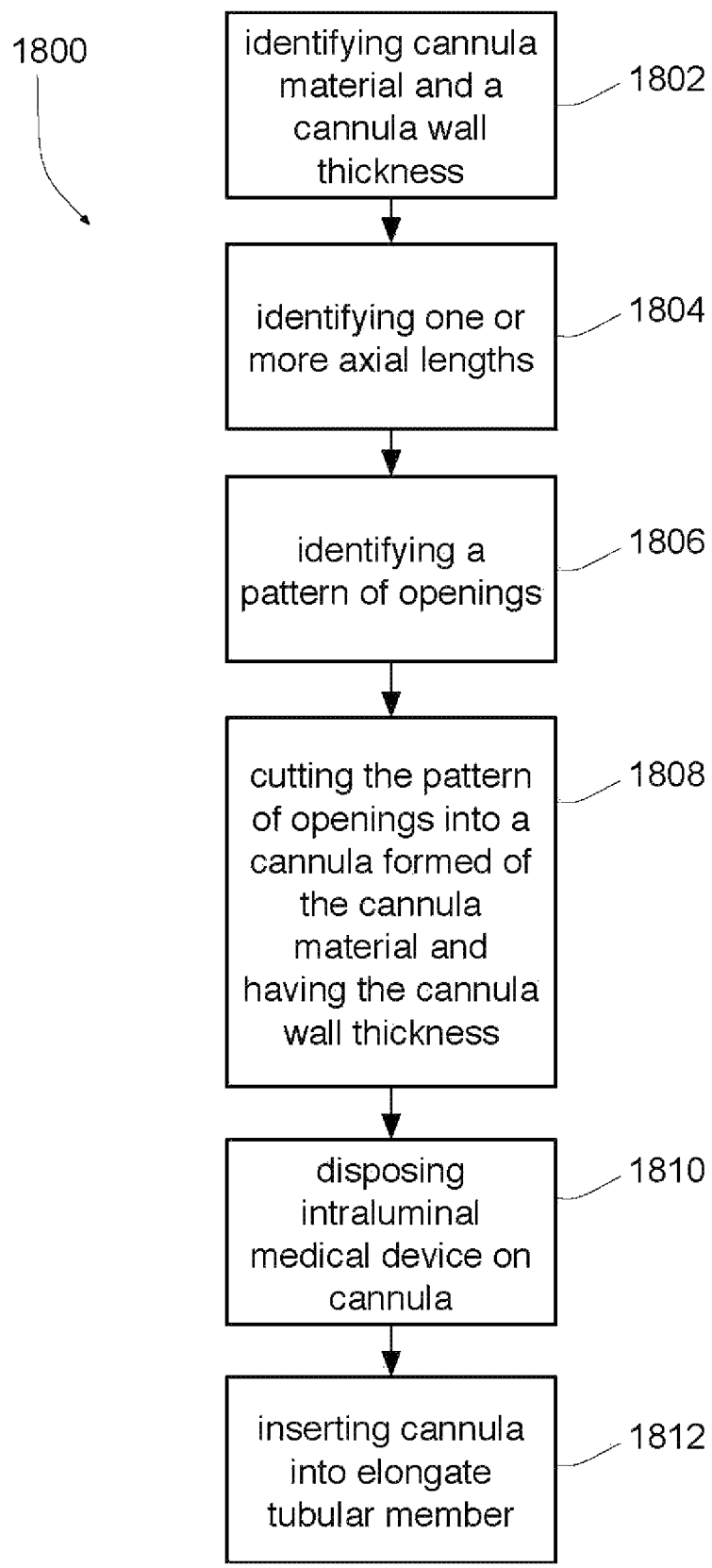
FIG. 23 is a flowchart representation of an example method of making a delivery system.

FIG. 23 illustrates an example method 1800 of making a delivery system. A first step 1802 comprises identifying a cannula material and a cannula wall thickness that provides a desired global stiffness for said cannula. Another step 1804 comprises identifying one or more axial lengths of said cannula along which a localized stiffness, different from the desired global stiffness, is desired. Another step 1806 comprises identifying a pattern of openings that will provide the desired localized stiffness when cut into a cannula formed of the cannula material and having the cannula wall thickness. Another step 1808 comprises cutting the pattern of openings into a cannula formed of the cannula material and having the cannula wall thickness at axial positions that correspond to the one or more axial lengths. Another step 1810 comprises disposing an intraluminal medical device on a portion of the cannula that is free of the pattern of openings. Another step 1812 comprises inserting the cannula into an elongate tubular member defining a lumen such that the intraluminal medical device is circumferentially disposed about the cannula and within the lumen.

While the examples described above reference specific features of particular drawings, it is understood that the various elements and/or features described herein in connection with one particular embodiment can be combined with those of another without departing from the scope of the invention. Furthermore, the cannulae, delivery systems and methods described and illustrated herein are examples. As such, they are not intended to limit the scope of protection sought in any manner. Rather, they serve only to aid those skilled in the art to make apparatuses and to practice methods in accordance with the invention.

We claim:

1. A delivery system, comprising:
   an outer tubular member defining an outer tubular member lumen;
   a cannula disposed within the outer tubular member lumen, the cannula comprising:
     an elongate tubular member having a lengthwise axis and a circumferential wall extending between a proximal end and a distal end and defining an interior lumen;
     the elongate tubular member having an intermediate axial portion extending between a proximal axial portion that includes the proximal end and a distal axial portion that includes the distal end, the distal axial portion extending from the distal end toward the proximal end;
     a pattern of openings in the circumferential wall of the elongate tubular member, the pattern of openings comprising a plurality of openings arranged in an interrupted spiral that extends circumferentially along the intermediate axial portion of the elongate tubular member;
     wherein the distal axial portion is free of the pattern of openings and comprises an uninterrupted circumferential wall; and
     wherein the proximal axial portion is longer than the distal axial portion;
   an intraluminal medical device circumferentially disposed around the distal axial portion of the elongate tubular member and within the lumen of the outer tubular member, the intraluminal medical device having an intraluminal medical device proximal end and an intraluminal medical device distal end; and
   a pusher slidably disposed over the cannula and within the outer tubular member lumen, the pusher having a pusher proximal end and a pusher distal end, the pusher distal end disposed between the pusher proximal end and the intraluminal medical device proximal end.

2. The delivery system of claim 1, wherein the pusher distal end abuts the intraluminal medical device proximal end.

3. The delivery system of claim 1, wherein the pusher comprises a tubular member.

4. The delivery system of claim 1, wherein the proximal axial portion of the elongate tubular member is free of the pattern of openings and comprises an uninterrupted circumferential wall.

5. The delivery system of claim 1, further comprising a conical distal tip secured to the distal end of the elongate tubular member.

6. The delivery system of claim 1, further comprising a double-tapered distal tip secured to the distal end of the elongate tubular member;
   wherein the double-tapered distal tip has an outer diameter that is greater than an outer diameter of the elongate tubular member.

7. The delivery system of claim 1, wherein the elongate tubular member comprises a metal.

8. The delivery system of claim 7, wherein the metal comprises stainless steel.

9. The delivery system of claim 1, wherein the intraluminal medical device comprises a self-expandable medical device.

10. The delivery system of claim 9, wherein the intraluminal medical device comprises a stent.

11. The delivery system of claim 9, wherein the intraluminal medical device comprises a valve.

12. The delivery system of claim 1, wherein each opening of the plurality of openings comprises an elongate slit that extends through the circumferential wall of the elongate tubular member.

13. A delivery system, comprising:
    an outer tubular member defining an outer tubular member lumen;
    a cannula disposed within the outer tubular member lumen, the cannula comprising:
      an elongate tubular member having a lengthwise axis and a circumferential wall extending between a proximal end and a distal end and defining an interior lumen;
      the elongate tubular member having an intermediate axial portion extending between a proximal axial portion that includes the proximal end and a distal axial portion that includes the distal end, the distal axial portion extending from the distal end toward the proximal end; and
      a pattern of openings in the circumferential wall of the elongate tubular member, the pattern of openings comprising a plurality of openings arranged in an interrupted spiral that extends circumferentially along the intermediate axial portion of the elongate tubular member;
      wherein the proximal axial portion and the distal axial portion are free of the pattern of openings and comprise an uninterrupted circumferential wall; and
      wherein the proximal axial portion is longer than the distal axial portion;
    a self-expandable intraluminal medical device circumferentially disposed around the distal axial portion of the elongate tubular member and within the lumen of the outer tubular member, the intraluminal medical device having an intraluminal medical device proximal end and an intraluminal medical device distal end; and
    a tubular pusher slidably disposed over the cannula and within the outer tubular member lumen, the tubular pusher having a pusher distal end that abuts the intraluminal medical device proximal end.

14. The delivery system of claim 13, wherein the intraluminal medical device comprises a stent.

15. The delivery system of claim 13, wherein the intraluminal medical device comprises a valve.

16. The delivery system of claim 13, wherein each opening of the plurality of openings comprises an elongate slit that extends through the circumferential wall of the elongate tubular member.

17. A delivery system, comprising:
an outer tubular member defining an outer tubular member lumen;
a cannula disposed within the outer tubular member lumen, the cannula comprising:
an elongate tubular member having a lengthwise axis and a circumferential wall extending between a proximal end and a distal end and defining an interior lumen;
the elongate tubular member having an intermediate axial portion extending between a proximal axial portion that includes the proximal end and a distal axial portion that includes the distal end, the distal axial portion extending from the distal end toward the proximal end;
a pattern of openings in the circumferential wall of the elongate tubular member, the pattern of openings comprising a plurality of openings arranged in an interrupted spiral that extends circumferentially along the intermediate axial portion of the elongate tubular member; and
a double-tapered distal tip secured to the distal end of the elongate tubular member, the double-tapered distal tip having an outer diameter that is greater than an outer diameter of the elongate tubular member;
wherein the proximal axial portion and the distal axial portion are free of the pattern of openings and comprise an uninterrupted circumferential wall; and
wherein the proximal axial portion is longer than the distal axial portion;
a self-expandable intraluminal medical device circumferentially disposed around the distal axial portion of the elongate tubular member and within the lumen of the outer tubular member, the intraluminal medical device having an intraluminal medical device proximal end and an intraluminal medical device distal end; and
a tubular pusher slidably disposed over the cannula and within the outer tubular member lumen, the tubular pusher having a pusher distal end that abuts the intraluminal medical device proximal end.

18. The delivery system of claim 17, wherein each opening of the plurality of openings comprises an elongate slit that extends through the circumferential wall of the elongate tubular member.

19. The delivery system of claim 17, wherein the intraluminal medical device comprises a stent.

20. The delivery system of claim 17, wherein the intraluminal medical device comprises a valve.

* * * * *